US012724948B2

(12) United States Patent
Al-Shedivat et al.

(10) Patent No.: US 12,724,948 B2
(45) Date of Patent: Sep. 1, 2026

(54) TRAINING GENERATIVE MACHINE LEARNING MODELS FOR 3D MOLECULAR STRUCTURE PREDICTION USING ALIGNMENT OBJECTIVES

(71) Applicant: Genesis Molecular AI, Inc., Burlingame, CA (US)

(72) Inventors: Maruan Al-Shedivat, New York, NY (US); Kenneth Knute Leidal, Windham, NH (US); Arthur Deng, Stanford, CA (US); David Li-Bland, Oakland, CA (US)

(73) Assignee: Genesis Molecular AI, Inc., San Diego, CA (US)

( * ) Notice: Subject to any disclaimer, the term of this patent is extended or adjusted under 35 U.S.C. 154(b) by 0 days.

(21) Appl. No.: 19/060,902

(22) Filed: Feb. 24, 2025

(65) Prior Publication Data

US 2025/0364081 A1 Nov. 27, 2025

Related U.S. Application Data

(60) Provisional application No. 63/671,468, filed on Jul. 15, 2024, provisional application No. 63/649,250, (Continued)

(51) Int. Cl.
*G06F 30/27* (2020.01)
*G16B 15/00* (2019.01)
*G16B 40/00* (2019.01)

(52) U.S. Cl.
CPC ............ *G06F 30/27* (2020.01); *G16B 15/00* (2019.02); *G16B 40/00* (2019.02)

(58) Field of Classification Search
CPC ......... G06F 30/20; G06F 30/27; G16B 15/00; G16B 40/00; G06N 3/092; G06N 3/08; G06N 3/0475; G06N 3/04; G06N 3/047
See application file for complete search history.

(56) References Cited

U.S. PATENT DOCUMENTS

2022/0358373 A1 11/2022 Bucher et al.
2025/0252268 A1* 8/2025 Rossi .................. G06N 3/0895

OTHER PUBLICATIONS

Jin et al., "Unsupervised Protein-Ligand Binding Energy Prediction via Neural Euler's Rotation Equation," arXiv:2301.10814v2 [q-bio. BM] Dec. 12, 2023 (Year: 2023).*

(Continued)

*Primary Examiner* — Miranda M Huang
*Assistant Examiner* — Yao David Huang
(74) *Attorney, Agent, or Firm* — Fish & Richardson P.C.

(57) ABSTRACT

Methods, systems, and apparatus, including computer programs encoded on a computer storage medium, for training a generative model by a machine learning training technique using an alignment objective. In one aspect, a method comprises, at each of a sequence of training steps: obtaining data characterizing a set of one or more molecules for the training step; processing, by the generative model, the data characterizing the set of one or more molecules to generate a plurality of alternative predicted 3D structures of the set of one or more molecules; and determining a respective alignment score for each of the plurality of alternative predicted 3D structures of the set of one or more molecules for the training step; and training the set of generative model parameters of the generative model to optimize the alignment objective.

20 Claims, 13 Drawing Sheets

MODULAR STRUCTURE PREDICTION SYSTEM 100

Related U.S. Application Data filed on May 17, 2024, provisional application No. 63/557,394, filed on Feb. 23, 2024.

(56) References Cited

OTHER PUBLICATIONS

Go et al., "Aligning Language Models with Preferences through f-divergence Minimization," arXiv:2302.08215v2 [cs.CL] Jun. 6, 2023 (Year: 2023).*

Ziegler et al., "Fine-Tuning Language Models from Human Preferences," arXiv:1909.08593v2 [cs.CL] Jan. 8, 2020 (Year: 2020).*

Dong et al., "RAFT: Reward rAnked FineTuning for Generative Foundation Model Alignment," arXiv:2304.06767v4 [cs.LG] Dec. 1, 2023 (Year: 2023).*

Amini et al., "Direct Preference Optimization with an Offset," arXiv:2402.10571v1 [cs.CL] Feb. 16, 2024 (Year: 2024).*

Park et al., "Preference Optimization for Molecular Language Models," arXiv:2310.12304v1 [stat.ML] Oct. 18, 2023 (Year: 2023).*

Zhou et al., "Antigen-Specific Antibody Design via Direct Energy-based Preference Optimization," arXiv:2403.16576v1 [q-bio.BM] Mar. 25, 2024 (Year: 2024).*

Kim et al., "Predicting chemical structure using reinforcement learning with a stack-augmented conditional variational autoencoder," Journal of Cheminformatics (2022) 14:83 (Year: 2022).*

Huang et al., "Binding-Adaptive Diffusion Models for Structure-Based Drug Design," Q-Bio, Jan. 2024, arXiv:2402.18583v1, 12 pages.

International Search Report and Written Opinion in International Appln. No. PCT/US2025/016976, mailed on May 26, 2025, 22 pages.

Jumper et al., "Highly accurate protein structure prediction with AlphaFold," Nature, Jul. 2021, 596(7873):583-589.

Lu et al., "DynamicBind: predicting ligand-specific protein-ligand complex structure with a deep equivariant generative model," Nature Communications, Feb. 15, 2024:1071, 13 pages.

Nakata et al., "End-to-end protein-ligand complex structure generation with diffusion-based generative models," BMC Bioinformatics, Jun. 24, 2023:233, 18 pages.

Qiao et al., "State-specific protein-ligand complex structure prediction with a multi-scale deep generative model," Q-Bio, Submitted on Apr. 2023, arXiv:2209.15171v2, 37 pages.

Qiao et al., "Supplementary information—State-specific protein-ligand complex structure prediction with a multi-scale deep generative model," Nature Machine Intelligence, Feb. 2024, 6(2):195-208, 25 pages.

Abramson et al., "Accurate Structure Prediction of Biomolecular Interactions with AlphaFold 3," Nature, May 8, 2024, 630:493-500.

Friesner et al., "Glide: a new approach for rapid, accurate docking and scoring. 1. Method and assessment of docking accuracy," Journal of Medicinal Chemistry, 2004, 47(7):1739-1749.

Morris et al., "AutoDock4 and AutoDockTools4: Automated docking with selective receptor flexibility," Journal of Computational Chemistry, 2009, 30(16):2785-2791.

Rafailov et al., "Direct Preference Optimization: Your Language Model is Secretly a Reward Model," 37th Conference on Neural Information Processing Systems (NeurIPS 2023), arXiv preprint, arXiv:2305.18290, May 2023, 27 pages.

Thomsen et al., "MolDock: a new technique for high-accuracy molecular docking," Journal of Medicinal Chemistry, 2006, 49(11):3315-3321.

Trott et al., "AutoDock Vina: improving the speed and accuracy of docking with a new scoring function, efficient optimization, and multithreading," Journal of Computational Chemistry, 2010, 31(2):455-461.

Watson et al., "De Novo Design of Protein Structure and Function with Rfdiffusion," Nature, Jul. 11, 2023, 620:1089-1100.

Zhang et al., "Adding Conditional Control to Text-to-Image Diffusion Models," Proceedings of the IEEE/CVF International Conference on Computer Vision (ICCV), 2023, pp. 3836-3847.

* cited by examiner

MODULAR STRUCTURE PREDICTION SYSTEM 100

EXAMPLE TORSION ANGLE

EXAMPLE PROCESS FOR GENERATING PREDICTED 3D STRUCTURE FOR MOLECULE SYSTEM

TRAINING A STRUCTURE PREDICTION GENERATIVE MODEL

TRAINING A PHYSICS PREDICTION NEURAL NETWORK

EXAMPLE PROCESS FOR TRAINING A STRUCTURE PREDICTION GENERATIVE MODEL

EXAMPLE PROCESS FOR DETERMINING ALIGNMENT LOSS FOR STRUCTURE PREDICTION GENERATIVE MODEL

EXAMPLE PROCESS FOR TRAINING A PHYSICS PREDICTION NEURAL NETWORK

EXAMPLE PROCESS FOR JOINTLY TRAINING PROTEIN GENERATIVE MODEL, LIGAND GENERATIVE MODEL, AND PROTEIN-LIGAND GENERATIVE MODEL

TRAINING GENERATIVE MACHINE LEARNING MODELS FOR 3D MOLECULAR STRUCTURE PREDICTION USING ALIGNMENT OBJECTIVES

CROSS-REFERENCE TO RELATED APPLICATIONS

This application claims the benefit of priority to U.S. Provisional Application No. 63/557,394, filed on Feb. 23, 2024, U.S. Provisional Application No. 63/649,250, filed on May 17, 2024, and U.S. Provisional Application No. 63/671,468, filed on Jul. 15, 2024, the contents of which are hereby incorporated by reference.

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that can predict a three-dimensional (3D) atomic structure of a complex that includes a protein and a ligand.

Throughout this specification, a "protein" refers to a biomolecule (or a complex of biomolecules) that includes one or more chains of amino acid residues. Proteins perform a vast array of functions within organisms, including catalyzing metabolic reactions, DNA replication, responding to stimuli, and transporting molecules from one location to another. Proteins vary in structure and function, and their 3D structure and function depends on the specific sequences of amino acids included in the protein.

Throughout this specification, a "ligand" refers to a molecule that can bind to a specific site on a protein, e.g., to form a complex with the protein. The binding typically involves interactions of various types, including ionic bonds, hydrogen bonds, and van der Waals forces. Ligands include substrates, inhibitors, activators, and signal-transducing molecules and can be of various sizes, ranging from small ions and molecules to large macromolecules. Ligands can be, e.g., small molecules, or proteins, or DNA molecules, or RNA molecules, or any other appropriate type of molecule.

According to a first aspect, there is provided a method performed by one or more computers, the method comprising: receiving data characterizing a protein and a ligand; processing a model input characterizing the protein, using a protein generative machine learning model, to generate a model output that includes data characterizing an initial predicted three-dimensional (3D) structure of the protein; processing a model input characterizing the ligand, using a ligand generative machine learning model, to generate a model output that includes data characterizing an initial predicted 3D structure of the ligand; processing a model input comprising: (i) the data characterizing the initial predicted 3D structure of the protein, and (ii) the data characterizing the initial predicted 3D structure of the ligand, using a protein-ligand generative machine learning model, to generate a model output that defines a predicted 3D structure of a complex comprising the protein and the ligand; and outputting the predicted 3D structure of the protein and the ligand.

In some implementations, processing the model input comprising: (i) the data characterizing the initial predicted 3D structure of the protein, and (ii) the data characterizing the initial predicted 3D structure of the ligand, using the protein-ligand generative machine learning model, to generate the model output that defines the predicted 3D structure of the complex comprising the protein and the ligand comprises: sampling, by the protein-ligand generative machine learning model, the predicted 3D structure of the complex comprising the protein and the ligand from a distribution over a space of possible 3D protein-ligand structures, wherein the distribution over the space of possible 3D protein-ligand structures is conditionally generated by the protein-ligand generative machine learning model in accordance with values of a set of protein-ligand generative machine learning model parameters.

In some implementations, the protein-ligand generative machine learning model has been trained by a machine learning training technique on a set of protein-ligand training examples that each correspond to a respective protein-ligand pair and include data comprising: (i) an amino acid sequence of a protein and a chemical structure of a ligand, and (ii) a 3D structure of a complex comprising the protein and the ligand.

In some implementations, for a plurality of the protein-ligand training examples, the 3D structure of the complex comprising the protein and the ligand is computationally generated.

In some implementations, for a plurality of the protein-ligand training examples, the 3D structure of the complex comprising the protein and the ligand is generated by molecular docking.

In some implementations, for one or more of the protein-ligand training examples, the 3D structure of the complex comprising the protein and the ligand is generated by a molecular dynamics (MD) simulation.

In some implementations, for a plurality of the protein-ligand training examples, the 3D structure of the complex comprising the protein and the ligand is derived from physical experiments.

In some implementations, for a plurality of the protein-ligand training examples, the 3D structure of the complex comprising the protein and the ligand is derived from x-ray crystallography.

In some implementations, for a plurality of the protein-ligand training examples, the 3D structure of the complex comprising the protein and the ligand is derived from cryo-electron microscopy (cryo-EM).

In some implementations, the protein-ligand generative machine learning has been trained by operations comprising: pre-training the protein-ligand generative machine learning model on a plurality of protein-ligand training examples wherein the 3D structure of the complex comprising the protein and the ligand is computationally generated; and fine-tuning the protein-ligand generative machine learning model on a plurality of protein-ligand training examples wherein the 3D structure of the complex comprising the protein and the ligand is derived from physical experiments.

In some implementations, processing the model input characterizing the protein, using the protein generative machine learning model, to generate a model output that includes data characterizing an initial predicted 3D structure of the protein comprises: sampling, by the protein generative machine learning model, the initial predicted 3D structure of the protein from a distribution over a space of possible 3D protein structures, wherein the distribution over the space of possible 3D protein structures is conditionally generated by the protein generative machine learning model in accordance with values of a set of protein generative machine learning model parameters; or generating, by the protein generative machine learning model, a latent representation of the initial predicted 3D structure of the protein, and providing the latent representation of the initial predicted 3D structure of the protein as the model output of the protein generative machine learning model.

In some implementations, the protein generative machine learning model has been trained on a set of protein training examples that each correspond to a respective protein and include data comprising: (i) an amino acid sequence of the protein, and (ii) a 3D structure of the protein.

In some implementations, for each of a plurality of protein training examples in the set of protein training examples, the 3D structure of the protein that is included in the training example defines a 3D structure of the protein in an unbound state.

In some implementations, for a plurality of the protein training examples, the 3D structure of the protein is computationally generated.

In some implementations, for a plurality of the protein training examples, the 3D structure of the protein is generated by a molecular dynamics simulation.

In some implementations, for a plurality of the protein training examples, the 3D structure of the protein is generated by a quantum mechanics simulation.

In some implementations, for a plurality of the protein training examples, the 3D structure of the protein is derived from physical experiments.

In some implementations, for a plurality of the protein training examples, the 3D structure of the protein is derived from x-ray crystallography.

In some implementations, for a plurality of the protein training examples, the 3D structure of the protein is derived from cryo-electron microscopy (cryo-EM).

In some implementations, the protein generative machine learning has been trained by operations comprising: pre-training the protein generative machine learning model on a plurality of protein training examples wherein the 3D structure of the protein is computationally generated; and fine-tuning the protein generative machine learning model on a plurality of protein training examples wherein the 3D structure of the protein is derived from physical experiments.

In some implementations, the model input characterizing the protein comprises data defining one or more amino acid sequence of the protein.

In some implementations, processing the model input characterizing the ligand, using the ligand generative machine learning model, to generate a model output that includes data characterizing an initial predicted 3D structure of the ligand comprises: sampling, by the ligand generative machine learning model, the initial predicted 3D structure of the ligand from a distribution over a space of possible 3D ligand structures, wherein the distribution over the space of possible 3D ligand structures is conditionally generated by the ligand generative machine learning model in accordance with values of a set of ligand generative machine learning model parameters; or generating, by the ligand generative machine learning model, a latent representation of the initial predicted 3D structure of the ligand, and providing the latent representation of the initial predicted 3D structure of the ligand as the model output of the ligand generative machine learning model.

In some implementations, the ligand generative machine learning model has been trained on a set of ligand training examples that each correspond to a respective ligand and include data comprising: (i) a chemical structure of the ligand, and (ii) a 3D structure of the ligand.

In some implementations, for a plurality of the ligand training examples, the 3D structure of the ligand is computationally generated.

In some implementations, for a plurality of the ligand training examples, the 3D structure of the ligand is generated by a molecular dynamics simulation.

In some implementations, for a plurality of the ligand training examples, the 3D structure of the ligand is generated by a quantum mechanics simulation.

In some implementations, for a plurality of the ligand training examples, the 3D structure of the ligand is derived from physical experiments.

In some implementations, for a plurality of the ligand training examples, the 3D structure of the ligand is derived from x-ray crystallography.

In some implementations, for a plurality of the ligand training examples, the 3D structure of the ligand is derived from cryo-electron microscopy (cryo-EM).

In some implementations, the ligand generative machine learning has been trained by operations comprising: pre-training the ligand generative machine learning model on a plurality of ligand training examples wherein the 3D structure of the ligand is computationally generated; and fine-tuning the ligand generative machine learning model on a plurality of ligand training examples wherein the 3D structure of the ligand is derived from physical experiments.

In some implementations, the model input characterizing the ligand comprises data defining a chemical structure of the ligand.

In some implementations, the ligand is a small molecule.

In some implementations, processing the model input comprising: (i) the data characterizing the initial predicted 3D structure of the protein, and (ii) the data characterizing the initial predicted 3D structure of the ligand, using the protein-ligand generative machine learning model, to generate the model output that defines the predicted 3D structure of the complex comprising the protein and the ligand comprises: generating an noisy 3D structure of the complex comprising the protein and the ligand; and denoising the noisy 3D structure of the complex comprising the protein and the ligand, over a sequence of one or more denoising iterations and in accordance with values of a set of protein-ligand generative machine learning model parameters, to generate the predicted 3D structure of the complex comprising the protein and the ligand.

In some implementations, denoising the noisy 3D structure of the complex comprising the protein and the ligand, over the sequence of one or more denoising iterations and in accordance with values of the set of protein-ligand generative machine learning model parameters, to generate the predicted 3D structure of the complex comprising the protein and the ligand comprises: performing a denoising process over a set of structure parameters that jointly parameterize the 3D structure of the complex comprising the protein and the ligand.

In some implementations, the protein-ligand generative machine learning model is a diffusion generative model; and performing the denoising process over the set of structure parameters that jointly parameterize the 3D structure of the complex comprising the protein and the ligand comprises performing a reverse diffusion process over the set of structure parameters.

In some implementations, the protein-ligand generative machine learning model is a flow based generative model; and performing the denoising process over the set of structure parameters that jointly parameterize the 3D structure of the complex comprising the protein and the ligand comprises determining, using differential equations specified by the flow based generative model, denoising trajectories for the set of structure parameters.

In some implementations, the set of structure parameters that jointly parametrize the 3D structure of the complex comprising the protein and the ligand comprise a plurality of backbone torsion angles of the protein.

In some implementations, the set of structure parameters that jointly parametrize the 3D structure of the complex comprising the protein and the ligand comprise a plurality of side chain torsion angles of the protein.

In some implementations, the set of structure parameters that jointly parametrize the 3D structure of the complex comprising the protein and the ligand comprise a plurality of translational, rotational, and torsional parameters of the ligand.

In some implementations, denoising the noisy 3D structure of the complex comprising the protein and the ligand comprises, at each denoising iteration in the sequence of one or more denoising iterations: receiving a current noisy 3D structure of the complex comprising the protein and the ligand; processing a network input that is derived from the current noisy 3D structure of the complex comprising the protein and the ligand using a denoising neural network to generate a denoising output; and updating the current noisy 3D structure of the complex comprising the protein and the ligand using the denoising output of the denoising neural network;

In some implementations, denoising the noisy 3D structure of the complex comprising the protein and the ligand further comprises, at one or more denoising iterations of the sequence of denoising iterations: providing the current noisy 3D structure of the complex comprising the protein and the ligand for processing at a next denoising iteration in the sequence of denoising iterations.

In some implementations, at each denoising iteration in the sequence of one or more denoising iterations, updating the current noisy 3D structure of the complex comprising the protein and the ligand using the denoising output of the denoising neural network comprises: generating a current predicted structure of the complex comprising the protein and the ligand based on the denoising output of the denoising neural network; and updating the current noisy 3D structure of the complex comprising the protein and the ligand by applying a diffusion sampling technique to a set of structure parameters that parametrize the current predicted structure of the complex comprising the protein and the ligand.

In some implementations, at each denoising iteration in the sequence of one or more denoising iterations, generating a current predicted structure of the complex comprising the protein and the ligand based on the denoising output of the denoising neural network comprises: processing data derived from the current noisy 3D structure of the complex comprising the protein and the ligand using an energy function to generate an energy of the current noisy 3D structure of the complex comprising the protein and the ligand; and generating the current predicted structure of the complex comprising the protein and the ligand based on both: (i) the denoising output, and (ii) the energy of the complex comprising the protein and the ligand.

In some implementations, processing data derived from the current noisy 3D structure of the complex comprising the protein and the ligand using the energy function to generate the energy of the current noisy 3D structure of the complex comprising the protein and the ligand comprises: determining a respective bond length of each of a plurality of bonds in the complex comprising the protein and the ligand; and generating the energy of the current noisy 3D structure of the complex comprising the protein and the ligand based at least in part on the respective bond lengths of the plurality of bonds.

In some implementations, generating the energy of the current noisy 3D structure of the complex comprising the protein and the ligand based at least in part on the respective bond lengths of the plurality of bonds comprises: determining, for each of the plurality of bonds, an energy associated with the bond as an energy of a spring having a predefined spring force that is extended to a length defined by the bond length from a predefined length at rest; and generating the energy of the current noisy 3D structure of the complex comprising the protein and the ligand based at least in part on the energies associated with the bonds.

In some implementations, for each of the plurality of bonds, the predefined length at rest is an expected length of the bond.

In some implementations, at each denoising iteration in the sequence of one or more denoising iterations, generating the current predicted structure of the complex comprising the protein and the ligand based on both: (i) the denoising output, and (ii) the energy of the complex comprising the protein and the ligand comprises: determining, for each structure parameter in a set of structure parameters that jointly parameterize the current noisy 3D structure of the complex comprising the protein and the ligand, a gradient of the energy with respect to a current value of the parameter; and determining, for each structure parameter in the set of structure parameters, an updated value of the structure parameter based on: (i) the gradient of the energy with respect to the current value of the structure parameter, and (ii) the denoising output; wherein the updated values of the structure parameters in the set of structure parameters define the current predicted structure of the complex comprising the protein and the ligand.

In some implementations, determining, for each structure parameter in the set of structure parameters, the updated value of the structure parameter based on: (i) the gradient of the energy with respect to the current value of the structure parameter, and (ii) the denoising output, comprises, for each structure parameter in the set of structure parameters: determining the updated value of the structure parameter as a linear combination of: (i) the gradient of the energy with respect to the current value of the structure parameter, and (ii) a correction value specified by the denoising output for the structure parameter.

In some implementations, the denoising neural network has been jointly trained with a physics prediction neural network that comprises a plurality of neural network layers; wherein the physics prediction neural network is configured to process a network input that characterizes an atomic system comprising a plurality of atoms to generate a network output that defines one or more predicted properties of the atomic system; and wherein the denoising neural network and the physics prediction neural network share respective parameter values of one or more shared neural network layers that are included in both the denoising neural network and the physics prediction neural network.

In some implementations, the physics prediction neural network generates a network output that defines a predicted energy of the atomic system.

In some implementations, the physics prediction neural network generates a network output that defines, for each of the plurality of atoms in the atomic system, a predicted force vector defining a predicted force on the atom.

In some implementations, the network input to the physics prediction neural network includes data specifying a 3D spatial coordinate in the atomic system; and wherein the network output of the physics prediction neural network defines a predicted electron density at the 3D spatial coordinate in the atomic system.

In some implementations, the physics prediction neural network is trained on a set of physics training examples, wherein each physics training example corresponds to a respective atomic system and comprises: (i) a training network input that characterizes the atomic system, and (ii) a target network output that defines one or more target properties of the atomic system.

In some implementations, training the physics prediction neural network on a physics training example from the set of physics training examples comprises: processing the training network input of the physics training example using the physics prediction neural network to generate a predicted network output that defines one or more predicted properties of the atomic system; determining gradients of an objective function with respect to a set of physics prediction neural network parameters, wherein the objective function measures a discrepancy between: (i) the one or more target properties of the atomic system specified by the physics training example and the one or more predicted properties of the atomic system generated by the physics prediction neural network; and updating values of the set of physics prediction neural network parameters using the gradients.

In some implementations, updating the values of the set of physics prediction neural network parameters using the gradients comprises: updating the values of the set of physics prediction neural network parameters that are included in the one or more shared neural network layers that are included in both the denoising neural network and the physics prediction neural network.

In some implementations, for a plurality of physics training examples from the set of physics training examples, the one or more target properties of the atomic system are determined by quantum mechanics calculations.

In some implementations, the method further comprises determining, based on the predicted 3D structure of the protein and the ligand, a binding score characterizing a binding affinity of the protein and the ligand.

In some implementations, the method further comprises selecting the protein, the ligand, or both for physical synthesis based at least in part on the binding score.

In some implementations, the method further comprises physically synthesizing the protein, the ligand, or both.

According to another aspect there is provided a method performed by one or more computers, the method comprising: obtaining data characterizing a protein and a set of ligands; determining, for each ligand in the set of ligands, a predicted joint 3D structure of the protein and the ligand using the methods described herein; determining, for each ligand in the set of ligands, a respective binding score characterizing a binding affinity of the protein and the ligand; and determining a ranking of the ligands in the set of ligands based on their respective binding scores.

In some implementations, determining, for each ligand in the set of ligands, the predicted joint 3D structure of the protein and the ligand using the methods described herein comprises: loading data characterizing the protein and the set of ligands into a local memory of a computing unit; and performing operations of the methods described herein for each ligand in the set of ligands substantially in parallel using the computing unit.

In some implementations, the computing unit comprises a graphics processing unit.

In some implementations, the method further comprises selecting one or more of the ligands for physical synthesis based on the ranking.

In some implementations, the method further comprises physically synthesizing the one or more selected ligands.

In some implementations, the method further comprises, for each of the one or more selected ligands, performing physical experiments to evaluate one or more properties of the selected ligand, wherein the one or more properties include one or more of: absorption properties, distribution properties, metabolism properties, excretion properties, or toxicity properties.

According to another aspect there is provided a method performed by one or more computers, the method comprising: obtaining data characterizing a ligand and a set of proteins; determining, for each protein in the set of proteins, a predicted joint 3D structure of the protein and the ligand using the methods described herein; determining, for each protein in the set of proteins, a respective binding score characterizing a binding affinity of the protein and the ligand; and determining a ranking of the proteins in the set of proteins based on their respective binding scores.

In some implementations, the method further comprises selecting one or more of the proteins for physical synthesis based on the ranking.

In some implementations, the method further comprises physically synthesizing the one or more selected proteins.

In some implementations, the method further comprises, for each of the one or more selected proteins, performing physical experiments to evaluate an experimental binding affinity of the selected protein and the ligand.

According to another aspect, there is provided a method performed by one or more computers, the method comprising: training a generative model by a machine learning training technique using an alignment objective, comprising, at each of a sequence of training steps: obtaining data characterizing a set of one or more molecules for the training step; processing, by the generative model and in accordance with current values of a set of generative model parameters of the generative model, the data characterizing the set of one or more molecules for the training step to generate a plurality of alternative predicted 3D structures of the set of one or more molecules for the training step; determining a respective alignment score for each of the plurality of alternative predicted 3D structures of the set of one or more molecules for the training step; and training the set of generative model parameters of the generative model to optimize the alignment objective, wherein the alignment objective depends on a target distribution of the alignment scores over the plurality of alternative predicted 3D structures of the set of one or more molecules for the training step; and providing the trained generative model.

In some implementations, the target distribution of the alignment scores over the plurality of alternative predicted 3D structures of the set of one or more molecules for the training step is defined by target likelihoods of the plurality of alternative predicted 3D structures of the set of one or more molecules for the training step; and for each of the plurality of alternative predicted 3D structures of the set of one or more molecules for the training step: the target likelihood for the predicted 3D structure comprises (i) a first term characterizing a likelihood of the generative model generating the predicted 3D structure and (ii) a second term characterizing the alignment score for the predicted 3D structure.

In some implementations, the first term characterizing the likelihood of the generative model generating the predicted 3D structure characterizes a likelihood of the generative model generating the predicted 3D structure by processing the data characterizing the set of one or more molecules for the training step in accordance with values of an initial set of generative model parameters.

In some implementations, the alignment objective measures an error between a first ranking and a second ranking of the plurality of alternative predicted 3D structures of the set of one or more molecules for the training step, wherein: the first ranking orders the plurality of alternative predicted 3D structures based on respective likelihoods of the generative model generating the predicted 3D structures by processing the data characterizing the set of one or more molecules for the training step in accordance with values of the current set of generative model parameters; and the second ranking orders the plurality of alternative predicted 3D structures based on the respective target likelihoods of the predicted 3D structures.

In some implementations, training the set of generative model parameters of the generative model to optimize the alignment objective comprises: determining a gradient of the alignment objective with respect to the current values of the set of generative model parameters; and updating the current values of the set of generative model parameters based on the gradient of the alignment objective.

In some implementations, for each of the plurality of alternative predicted 3D structures of the set of one or more molecules for the training step, the respective alignment score for the predicted 3D structure characterizes a predicted likelihood of experimentally observing the predicted 3D structure within a physical system that includes the set of one or more molecules for the training step.

In some implementations, for each of the plurality of alternative predicted 3D structures of the set of one or more molecules for the training step, the respective alignment score for the predicted 3D structure characterizes an energy of the predicted 3D structure.

In some implementations, the predicted 3D structure is a predicted 3D structure for a protein-ligand complex; and the energy of the predicted 3D structure is a binding energy of the protein-ligand complex.

In some implementations, determining the respective alignment score for each of the plurality of alternative predicted 3D structures of the set of one or more molecules for the training step comprises computationally simulating the predicted 3D structures to determine the energies of the predicted 3D structures.

In some implementations, for each of the plurality of alternative predicted 3D structures of the set of one or more molecules for the training step, the respective alignment score for the predicted 3D structure characterizes an estimated relative likelihood of the predicted 3D structure as determined by human feedback.

In some implementations, determining the respective alignment score for each of the plurality of alternative predicted 3D structures of the set of one or more molecules for the training step comprises: outputting data characterizing the plurality of alternative predicted 3D structures to a user; receiving human feedback from the user that characterizes estimated relative likelihoods of the predicted 3D structures; and determining the respective alignment scores based on the received human feedback.

In some implementations, the human feedback comprises numerical scores assigned by the user to the predicted 3D structures.

In some implementations, the human feedback comprises a ranking of the predicted 3D structures as determined by the user.

In some implementations, the data characterizing the set of one or more molecules for the training step characterizes a respective chemical composition of each molecule in the set of one or more molecules.

In some implementations, the set of one or more molecules for the training step includes a protein.

In some implementations, the data characterizing the set of one or more molecules for the training step includes an amino acid sequence of the protein.

In some implementations, the set of one or more molecules for the training step includes a ligand.

In some implementations, the data characterizing the set of one or more molecules for the training step includes a chemical structure of the ligand.

In some implementations, the set of one or more molecules for the training step comprises a protein-ligand complex.

In some implementations, the generative model has been trained by a machine learning training technique on a set of molecular structure training examples using a training objective; each molecular structure training example corresponds to a respective target set of one or more molecules and includes data comprising: (i) data characterizing chemical compositions of the set of one or more molecules, and (ii) a target 3D structure for the set of one or more molecules; and the training objective measures a difference between (i) a distribution of predicted 3D structures as generated by the generative model and (ii) a target distribution of 3D structures.

In some implementations, each molecular structure training example corresponds to a respective protein-ligand pair and include data comprising: (i) an amino acid sequence of a protein and a chemical structure of a ligand, and (ii) a 3D structure of a complex comprising the protein and the ligand.

In some implementations, for a plurality of the molecular structure training examples, the 3D structure of the complex comprising the protein and the ligand is computationally generated.

In some implementations, for a plurality of the molecular structure training examples, the 3D structure of the complex comprising the protein and the ligand is generated by molecular docking.

In some implementations, for one or more of the molecular structure training examples, the 3D structure of the complex comprising the protein and the ligand is generated by a molecular dynamics (MD) simulation.

In some implementations, for a plurality of the molecular structure training examples, the 3D structure of the complex comprising the protein and the ligand is derived from physical experiments.

In some implementations, for a plurality of the molecular structure training examples, the 3D structure of the complex comprising the protein and the ligand is derived from x-ray crystallography.

In some implementations, for a plurality of the molecular structure training examples, the 3D structure of the complex comprising the protein and the ligand is derived from cryo-electron microscopy (cryo-EM).

In some implementations, the generative model has been trained by on the set of molecular structure training examples using the training objective by operations comprising: pre-training the generative model on a plurality of molecular structure training examples wherein the 3D structure of the complex comprising the protein and the ligand is computationally generated; and fine-tuning the generative on a plurality of molecular structure training examples wherein the 3D structure of the complex comprising the protein and the ligand is derived from physical experiments.

In some implementations, the method further comprises: receiving data characterizing a protein and a ligand; processing, using the generative model and in accordance with the trained set of generative model parameters, a model input characterizing the protein, the ligand, or both, to generate a model output that includes data characterizing a respective predicted 3D structure; determining a predicted joint 3D structure of a complex comprising the protein and the ligand based on the generated model output; and outputting the predicted joint 3D structure of the protein and the ligand.

In some implementations, the method further comprises determining, based on the predicted joint 3D structure of the protein and the ligand, a binding score characterizing a binding affinity of the protein and the ligand.

In some implementations, the method further comprises selecting the protein, the ligand, or both for physical synthesis based at least in part on the binding score.

In some implementations, the method further comprises physically synthesizing the protein, the ligand, or both.

According to another aspect, there is provided a method comprising: obtaining data characterizing a protein and a set of ligands; determining, for each ligand in the set of ligands, a predicted joint 3D structure of the protein and the ligand using the methods described herein; determining, for each ligand in the set of ligands, a respective binding score characterizing a binding affinity of the protein and the ligand; and determining a ranking of the ligands in the set of ligands based on their respective binding scores.

In some implementations, determining, for each ligand in the set of ligands, the predicted joint 3D structure of the protein and the ligand comprises: loading data characterizing the protein and the set of ligands into a local memory of a computing unit; and performing operations of the methods described herein for each ligand in the set of ligands substantially in parallel using the computing unit.

In some implementations, the computing unit comprises a graphics processing unit.

In some implementations, the method further comprises selecting one or more of the ligands for physical synthesis based on the ranking.

In some implementations, the method further comprises physically synthesizing the one or more selected ligands.

In some implementations, the method further comprises, for each of the one or more selected ligands, performing physical experiments to evaluate one or more properties of the selected ligand, wherein the one or more properties include one or more of: absorption properties, distribution properties, metabolism properties, excretion properties, or toxicity properties.

In another aspect there is provided a method comprising: obtaining data characterizing a ligand and a set of proteins; determining, for each protein in the set of proteins, a predicted joint 3D structure of the protein and the ligand using the methods described herein; determining, for each protein in the set of proteins, a respective binding score characterizing a binding affinity of the protein and the ligand; and determining a ranking of the proteins in the set of proteins based on their respective binding scores.

In some implementations, the method further comprises selecting one or more of the proteins for physical synthesis based on the ranking.

In some implementations, the method further comprises physically synthesizing the one or more selected proteins.

In some implementations, the method further comprises, for each of the one or more selected proteins, performing physical experiments to evaluate an experimental binding affinity of the selected protein and the ligand.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect, there are provided one or more non-transitory computer storage media storing instructions that when executed by one or more computers cause the one or more computers to perform operations of the methods described herein.

The ability to predict the joint 3D structure of a complex involving a protein and a ligand is of significant utility in various fields, including drug discovery and development. Accurately predicting such structures enables a deeper understanding of the molecular basis of protein-ligand interactions, which is crucial for rational drug design. This predictive capability can aid in identifying the binding affinity and specificity of ligands towards protein targets, thus facilitating the development of more effective and selective therapeutic agents. Further, this predictive capability can contribute to the elucidation of biological pathways and mechanisms, offering insights into disease processes and potential treatment strategies. The system described in this specification can therefore contribute to accelerating the process of drug discovery.

For instance, drug discovery often involves identifying a protein that is involved in a disease process, and then searching for a ligand that will bind to the protein with high binding affinity in order to activate, inhibit, or alter the function of the protein to disrupt the disease pathway and achieve a therapeutic effect. Given a protein target, the system can be used to screen a library of candidate ligands based on their predicted binding affinity for the protein. More specifically, for each ligand in the library, the system can generate a respective predicted 3D structure of a complex that includes the protein and the ligand. The system can determine a respective predicted binding affinity for each ligand by evaluating the 3D structure of the complex that includes the protein and the ligand, e.g., using a mechanistic or machine learned scoring function. The system can then rank the candidate ligands based on their predicted binding affinity for the protein, and one or more of the candidate ligands can be selected for further development as potential drugs.

The system can generate a predicted 3D structure of a protein-ligand complex using a modular machine learning architecture that includes: (i) a protein generative machine learning model, (ii) a ligand generative machine learning model, and (iii) a protein-ligand generative machine learning model. The protein generative machine learning model can be configured to process data characterizing a protein to generate data characterizing a predicted 3D structure of the protein (e.g., a latent representation of the predicted 3D structure of the protein). The ligand generative machine learning model can be configured to process data characterizing a ligand to generate data characterizing a predicted 3D structure of the ligand (e.g., a latent representation of the predicted 3D structure of the ligand). The protein-ligand generative machine learning model can be configured to process data characterizing a predicted 3D structure of a protein (e.g., a latent representation of the predicted 3D structure of the protein) and data characterizing a predicted 3D structure of a ligand (e.g., a latent representation of the predicted 3D structure of the ligand) to generate a predicted 3D structure of the protein-ligand complex. Given a protein and a ligand, the system can thus generate data characterizing initial predicted 3D structures of the protein and the ligand using the protein generative machine learning model and the ligand generative machine learning model respectively. The system can then feed the data characterizing the predicted 3D structures of the protein and the ligand into the protein-ligand generative machine learning model to generate the predicted 3D structure of the protein-ligand complex.

The modular architecture of the system described in this specification can achieve several advantages compared to, e.g., an "integrated" architecture that directly maps data characterizing a protein and a ligand to a predicted 3D structure of the protein-ligand complex without the intermediate step of separately generating data characterizing the (unbound) protein structure and the ligand structure.

First, the modular architecture greatly expands the amount of training data available for training the system. In particular, the protein generative machine learning model can be trained on protein training examples that define 3D structures of proteins, the ligand generative machine learning model can be trained on ligand training examples that define 3D structures of ligands, and the protein-ligand generative machine learning model can be trained on protein-ligand training examples that define 3D structures of protein-ligand complexes. The training of the protein generative machine learning model and the ligand generative machine learning model can thus be performed (at least partially) independently of the training of the protein-ligand generative machine learning model using protein training examples and the ligand training examples which are significantly more plentiful and readily available than protein-ligand training examples. In contrast, an integrated architecture (as defined above) can only be trained on a much more limited training data set of protein-ligand training examples. The system described in this specification can thus achieve a higher accuracy and can generalize more effectively to previously unseen proteins and ligands than alternative systems, e.g., as a result of being trained on a larger set of training data (which is enabled by the modular architecture).

Further, the modular architecture of the system provides a technical solution to the technical problem of training data scarcity when training generative machine learning models to predict 3D structures of protein-ligand complexes. Training data scarcity is an issue in this setting because large quantities of training data are required for training such generative machine learning models, but relatively little experimental data exists characterizing 3D structures of protein-ligand complexes, e.g., because of the complexity and expense of performing physical experiments such as x-ray crystallography or nuclear magnetic resonance spectroscopy in order to physically measure 3D molecular structures. In the absence of sufficient training data, training a generative machine learning model to predict molecular structures may be infeasible, e.g., because the training may fail to converge. The modular architecture of the system described in this specification unlocks large quantities of additional training data, e.g., for the reasons described above, and therefore provides a technical solution to the problem of training data scarcity.

Second, the modular architecture natural encodes a useful inductive bias—namely, that the 3D structure of the protein-ligand complex will be informed by the (unbound) 3D structures of the protein and the ligand. Further, the individual tasks of predicting a protein structure, predicting a ligand structure, and predicting the structure of the protein-ligand complex (conditioned on the protein structure and the ligand structure) are each individually easier and less complex than directly predicting the structure of the protein-ligand complex. The machine learning models included in the modular architecture can thus have collectively simpler, lighter-weight architectures, and can be trained over fewer training iterations, as compared to an integrated architecture (i.e., that does not perform the intermediate steps of generating data characterizing predicted protein structures and ligand structures) with comparable prediction accuracy. The modular architecture thus enables reduced consumption of computational resources during training (e.g., by reducing the number of training iterations required to achieve an acceptable prediction accuracy) and during inference (e.g., by reducing the required complexity of the machine learning model architectures) compared to alternative systems. Computational resources can include, e.g., memory and computing power. The reduced usage of computational resources further enables training of larger and more powerful machine learning models on more training data using the same computational budget.

The protein-ligand generative machine learning model, as part of predicting the 3D structure of a protein-ligand complex, can generate values for a set of structure parameters that parametrize the 3D structure of the protein-ligand complex. The set of structure parameters can include a set of backbone torsion angles of the protein in addition to other structure parameters such as, e.g., rotational, translational, and torsional parameters of the ligand. The protein-ligand generative machine learning model can thus account for significant changes in the conformation of the protein related to the binding of the ligand, in particular, at the level of the protein backbone. In contrast, an alternative system that only generates values for ligand structure parameters while treating the protein structure as fixed, or that generates values for a more limited set of protein structure parameters excluding the backbone torsion angles, cannot account for the full breadth and scope of protein conformational changes associated with ligand binding. The system thus provides a technical solution (e.g., including adaptively predicting backbone torsion angles of the protein) to a technical problem that arises in performing predicting joint 3D structures of protein-ligand complexes, namely, accounting for the conformational changes in the protein resulting from the binding of the ligand.

The protein generative machine learning model, ligand generative machine learning model, and protein-ligand generative machine learning model can be implemented as generative models that can iteratively denoise an initial noisy predicted 3D structure of a respective molecule (e.g., a protein, a ligand, a protein-ligand complex, etc.) over a sequence of one or more denoising iterations. For example, any of the generative machine learning models (e.g., the protein generative machine learning model, the ligand generative machine learning model, the protein-ligand generative machine learning model) can be implemented as a diffusion model that can iteratively denoise the initial noisy predicted 3D structures using a reverse diffusion process. As another example, any of the generative machine learning models (e.g., the protein generative machine learning model, the ligand generative machine learning model, or the protein-ligand generative machine learning model) can be implemented as a flow-based model that can denoise the initial noisy predicted 3D structures for the model following a set of differential equations specified by the generative machine learning model.

The initial noisy predicted 3D structures for any of the generative machine learning models can be sampled from a distribution of over a space of possible structure parameter values (e.g., from a multivariate Gaussian distribution, a multivariate uniform distribution, etc.). Alternatively, the initial noisy predicted 3D structures for any of the generative machine learning models can be initial estimates for the 3D structures of the respective molecules. For example, an initial noisy predicted 3D structure for a molecule (e.g., a protein, ligand, protein-ligand complex, etc.) can be an initial estimate determined using crystallography of the molecule. As another example, an initial noisy predicted 3D structure for a ligand can be determined as an initial conformal isomer (e.g., a conformer) of the ligand. As another example, an initial noisy predicted 3D structure for a protein-ligand complex can be determined using initial estimates of unbound 3D structures for the protein and the ligand of the protein-ligand complex (e.g., as generated by the protein generative machine learning model and the ligand generative machine learning model, respectively). Utilizing initial estimates of molecule structures for the initial noisy predicted 3D structures can enable the generative machine learning models to generate denoised predicted 3D structures using fewer computational resources (e.g., using fewer denoising iterations, using simpler neural network architectures, etc.) and can therefore reduce consumption of computational resources during training and during inference compared to alternative systems.

In some cases, the protein-ligand generative machine learning model can be implemented to perform a denoising process over a constrained set of structure parameters (e.g., including protein and ligand torsion angles) that require the predicted 3D structure to maintain a plausible physical conformation at each denoising iteration. However, this approach can reduce the efficiency of the denoising process, e.g., by preventing the generation of non-physical intermediate structures as part of rapid global modifications (folds) in the structure as the noisy structure converges on a denoised structure. In other cases, the protein-ligand generative machine learning model can be implemented to perform a denoising process over a less constrained set of structure parameters (e.g., including 3D spatial positions of some or all of the atoms in the complex). However, this approach can require the protein-ligand generative machine learning model to operate over a very large number (e.g., thousands) of degrees of freedom, which can inhibit the training of the protein-ligand generative machine learning model (e.g., by requiring significantly more training data) and can prevent the protein-ligand generative machine learning model from effectively generalizing to unseen proteins and ligands.

To address these issues, the system can constrain and regularize the evolution of the set of structure parameters over the sequence of denoising iterations using an energy function that can associate an energy with a 3D structure of a protein-ligand complex. For instance, the energy function can assign an energy to a 3D structure of a protein-ligand complex that is proportional to the physical plausibility of the 3D structure, e.g., where 3D structures with non-physical (e.g., excessively large or small) bond lengths would be assigned higher energy values. At each denoising iteration, the system can adjust the current values of the set of structure parameters using gradients of the energy function, e.g., to impose a soft constraint that encourages (but does not require) the predicted 3D structure to have a physically plausible conformation. Constraining the denoising process using an energy function can allow the system to leverage the computational advantages of using a less constrained set of structure parameters that allow the 3D structure of the protein-ligand complex to assume non-physical conformations during certain intermediate steps of the diffusion process while mitigating associated risks during training and inference (as described above). In particular, constraining the reverse diffusion process using an energy function can enable reduced consumption of computational resources by increasing the likelihood that the denoising process will converge over fewer denoising iterations.

The system can jointly train the denoising neural network of the protein-ligand generative machine learning model with a physics prediction neural network that is configured to process data characterizing an atomic system to predict one or more physical properties of the atomic system, e.g., free energy, atomic forces, electron density, and so forth. In particular, the denoising neural network and the physics prediction neural network can share one or more neural network layers, such that adjusting the values of the parameters of the shared neural network layers during training of the physics prediction neural network has the effect of also modifying the shared parameters of the denoising neural network. Jointly training the denoising neural network and the physics prediction neural network can improve the performance of the denoising neural network while reducing the amount of training data and the number of training iterations required for training the denoising neural network (thus reducing consumption of computational resources during training). Further, training data for training the physics prediction neural network (and, by extension, the denoising neural network) may be significantly more plentiful and readily available than the protein-ligand training examples for training the denoising neural network directly.

The system can train the protein generative machine learning model, the ligand generative machine learning model, and the protein-ligand generative machine learning model, on both real-world training examples (with 3D structures derived from physical experiments) and synthetic training examples (with 3D structures derived using computational methods). For instance, the system can pre-train the generative machine learning models on synthetic training examples, and then finetune the generative machine learning models on real training examples (or on a blend of real training examples and synthetic training examples). Synthetic training examples can be generated using significantly fewer resources than real-world training examples, and can be used to significantly augment the amount of training data available for training the generative machine learning models.

Training a generative machine learning model (e.g., the protein generative machine learning model, the ligand generative machine learning model, the protein-ligand generative machine learning model, etc.) to generate physically plausible 3D structures can require a very large number of training examples. In order to increase the physical plausibility of the generated 3D structures while using fewer training examples, the system can train (e.g., fine-tune) the generative models using an alignment objective that measures a physical plausibility of the generated 3D structures. The alignment objective can encourage the generative models to generate 3D structures in accordance with a target distribution of alignment scores assigned to the generated 3D structures.

In some implementations, the alignment objective can be based on a ranking of generated 3D structures by a measure of physical plausibility. An example alignment objective is the Direct Preference Optimization (DPO) objective described by Rafailov et al. in "Direct Preference Optimization: Your Language Model is Secretly a Reward Model".

The alignment scores can be any of a variety of measures for the physical plausibility of the generated 3D structures. As an example, the alignment score can be a physical characteristic of the 3D structures (e.g., an energy of the 3D structures), and the alignment objective can encourage the generative models to generate 3D structures in accordance with a physically plausible distribution of the physical characteristic. As another example, the alignment score can be generated by human feedback (e.g., as determined by an expert providing a score characterizing a plausibility of the generated 3D structure), and the alignment objective can encourage the generative models to generate physically plausible 3D structures as judged by human (e.g., expert) feedback.

Fine-tuning using the alignment objective allows the system to more directly optimize the generative machine learning models to generate physically plausible 3D structures. Conventional methods for training generative machine learning models that do not utilize fine-tuning with an alignment objective require large training data sets of physically plausible 3D structures in order to train the generative machine learning models to generate physically plausible 3D structures by example. Fine-tuning with the alignment objective enables the system to update the generative machine learning models using direct feedback regarding the physical plausibility of generated 3D structures and can therefore enable the system to train the generative models using fewer resources (e.g., using fewer training examples, in less training time, etc.) compared to conventional methods.

Fine-tuning using the alignment objective can also reduce the computational cost of generating physically plausible 3D structures at inference time. For example, in comparison to conventional methods that can require generating and screening large numbers of predicted 3D structures to obtain a physically plausible 3D structure, a generative machine learning model fine-tuned with the alignment objective can directly generate physically plausible 3D structures.

Further, fine-tuning with the alignment objective contributes to a technical solution to the technical problem of training data scarcity when training generative machine learning models to predict 3D structures of protein-ligand complexes. In particular, alignment scores can be determined for training examples already obtained for training the generative machine learning models and can therefore provide an additional training signal for the generative machine learning models without requiring additional training examples. Fine-tuning the generative machine learning models with the alignment objective can therefore contribute to a technical solution to the problem of training data scarcity by enabling training the generative machine learning models to attain better performance (e.g., to achieve greater desired accuracies, generate more physically plausible predicted structures, etc.) which obtaining, storing, and training on additional training examples.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
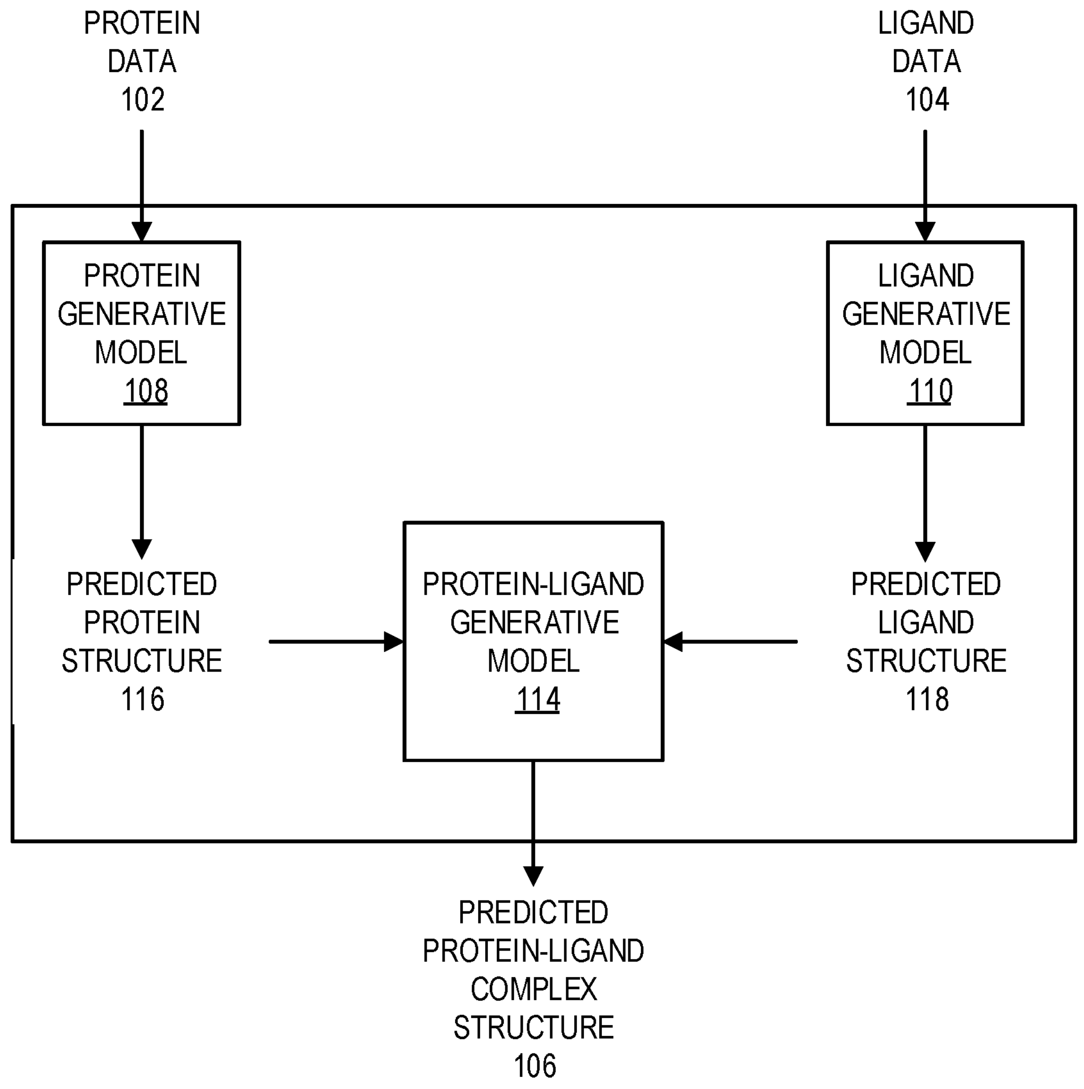
FIG. 1 is a block diagram of an example modular structure prediction system.

FIG. 1 shows an example modular structure prediction system 100. The modular structure prediction system 100 is an example of a system implemented as computer programs on one or more computers in one or more locations in which the systems, components, and techniques described below are implemented.

The modular structure prediction system 100 can process protein data 102 characterizing a protein and ligand data 104 characterizing a ligand to generate a predicted three-dimensional (3D) structure 106 for a protein-ligand complex that includes the protein and the ligand.

The ligand data 102 can characterize any of a variety of ligands. As an example, the ligand data 102 can characterize a small molecule ligand (e.g., a ligand that is a non-polymer organic molecule with a low molecular weight, e.g., <900 Daltons). As another example, the ligand data 102 can characterize a poly-peptide ligand that is, itself, a protein. As another example, the ligand data 102 can characterize a nucleic acid (e.g., a ribonucleic acid (RNA), a deoxyribonucleic acid (DNA), and so on).

The modular structure prediction system 100 includes a protein generative model 108, a ligand generative model 110, and a protein-ligand generative model 112, which are described next (and throughout this specification).

The protein generative model 108, the ligand generative model 110, and the protein-ligand generative model 112 can each be structure prediction generative models configured to process data characterizing respective types of molecules and conditionally generate predicted 3D structures for the respective types of molecules. In particular, the protein generative model 108 can be configured (e.g., trained) to process data characterizing proteins to generate predicted 3D structures for the proteins and the ligand generative model 110 can be configured (e.g., trained) to process data characterizing ligands to generate predicted 3D structures for the ligands. The protein generative model 108 and the ligand generative model 110 can be configured to generate predicted 3D structures for respective unbound proteins and ligands.

The protein-ligand generative model 112 can be configured (e.g., trained) to process data characterizing a pair of a protein and a ligand to generate a predicted joint 3D structure for the protein and the ligand (e.g., a predicted 3D structure of a protein-ligand complex that includes the protein and the ligand). In particular, the protein-ligand generative model 112 can be configured to process data characterizing initial predicted 3D structures for the protein and the ligand (e.g., as generated by the protein generative model 108 and the ligand generative model 110).

The architecture and training of the structure prediction generative models (e.g., the protein generative model 108, the ligand generative model 110, and the protein-ligand generative model 112) are described in more detail below with reference to FIGS. 3-6.

The modular structure prediction system 100 can therefore generate the predicted three-dimensional (3D) structure 106 for the protein-ligand complex by processing the protein data 102 characterizing the protein using the protein generative model 108 to generate data characterizing an initial predicted 3D structure 116 for the protein, processing the ligand data 104 characterizing the ligand using the ligand generative model 110 to generate data characterizing an initial predicted 3D structure 118 for the ligand, and then processing both the initial predicted protein structure data 116 and the initial predicted ligand structure data 118 using the protein-ligand generative model 112 to generate the predicted three-dimensional (3D) structure 106 for the protein-ligand complex of the protein and the ligand.

An example process for generating the predicted three-dimensional (3D) structure 106 for the protein-ligand complex of the protein and the ligand is described in more detail below with reference to FIG. 2.

In some implementations, the protein generative model 108 and the ligand generative model 110 can be separate generative models configured (e.g., trained) to generate predicted 3D structures for proteins and ligands, respectively. In other implementations, the protein generative model 108 and the ligand generative model 110 can be a same, combined generative model that is configured (e.g., trained) to generate to generate predicted 3D structures for both proteins and ligands. In particular, the combined protein generative model 108 and ligand generative model 110 can be configured to generate the initial predicted 3D structure 116 for the protein by processing the protein data 102 and to also generate the initial predicted 3D structure 118 for the ligand by processing the ligand data 104.

The protein generative model 108, the ligand generative model 110, and the protein-ligand generative model 112 can be individually trained (e.g., pre-trained) to conditionally generate predicted 3D structures for the respective types of molecules, as described in more detail below with respect to FIG. 7. When the protein generative model 108 and the ligand generative model 110 are separate generative models, the protein generative model 108 and the ligand generative model can be separately trained (e.g., pre-trained) to conditionally generate predicted 3D structures for proteins and ligands, respectively. When the protein generative model 108 and the ligand generative model are a same, combined generative model, the combined protein generative model 108 and ligand generative model 110 can be trained (e.g., pre-trained) to conditionally generate predicted 3D structures for both proteins and ligands using training data that includes example proteins and example ligands.

In some implementations, the protein generative model 108, the ligand generative model 110, and the protein-ligand generative model 112 can be jointly trained (e.g., fine-tuned) to generate predicted 3D structures for protein-ligand complexes. An example process of jointly training (e.g., fine-tuning) the protein generative model 108, the ligand generative model 110, and the protein-ligand generative model 112 is described in more detail below with reference to FIG. 10.

By generating the initial predicted protein structure 116 using the protein generative model 108 and the initial predicted ligand structure 118 using the ligand generative model 110 as part of generating the predicted 3D structure 106 for the protein-ligand complex of the protein and the ligand, the modular structure prediction system 100 can achieve several advantages compared to, e.g., a conventional "integrated" prediction system configured to directly predict a 3D structure of the protein-ligand complex based on the protein data 102 and the ligand data 104 without performing the intermediate step of separately generating data characterizing the initial predicted (unbound) protein structure 116 and ligand structure 118.

First, individually training (e.g., pre-training) the protein generative model 108, the ligand generative model 110, and the protein-ligand generative model 112 to generate predicted structures for their respective types of molecules can greatly expand the amount of training data available for training the system 100. In particular, the protein generative model 108 and the ligand generative model 110 can be trained (e.g., pre-trained) independently of the protein-ligand generative model 112 using training examples of unbound proteins and ligands, which are significantly more plentiful and readily available training examples of bound protein-ligand complexes. In contrast, a conventional "integrated" architecture can only be trained on a much more limited training data set of example bound protein-ligand complexes. With more training data compared to conventional "integrated" architectures, the system 100 can thus achieve a higher accuracy and can generalize more effectively to previously unseen proteins and ligands than conventional systems.

Second, generating the predicted 3D structure 106 for the protein-ligand complex of the protein and the ligand based on the initial predicted protein structure 116 and the initial predicted ligand structure 118 can be an easier prediction task compared to directly generating the structure 106 for the protein-ligand complex based only on the protein data 102 and the ligand data 104. Separately performing the individual tasks of predicting the initial protein structure 116, predicting the initial ligand structure 118, and predicting the structure of the protein-ligand complex 106 (conditioned on the initial protein structure 116 and the initial ligand structure 118) can be easier and less complex than directly predicting the structure of the protein-ligand complex 106. This enables the protein generative model 108, the ligand generative model 110, and the protein-ligand generative model 112 to collectively have simpler, lighter-weight architectures, and be trained over fewer training iterations compared to conventional "integrated" architectures with comparable prediction accuracy. The modular structure prediction system 100 can therefore be trained and can perform inference using fewer computational resources than conventional "integrated" architectures.

The modular structure prediction system 100 can therefore more efficiently generate predicted 3D structures for protein-ligand complexes for use in any of a variety of down-stream tasks. As an example, the system 100 can efficiently generate and process a predicted 3D structure for a protein-ligand complex to determine a binding score that characterizes a binding affinity of the protein and the ligand. The system 100 can then select the protein, the ligand, or both for physical synthesis (e.g., to perform physical experiments using synthesized samples of the protein, the ligand, or both) based on the binding score. As another example, as described in more detail below with reference to FIG. 11 and FIG. 12, the system 100 can efficiently screen sets of candidate ligands and candidate proteins based on predicted 3D structures for protein-ligand complexes that include the candidate ligands and proteins (e.g., by evaluating and ranking binding scores for the candidate ligands and proteins).

Figure 2:
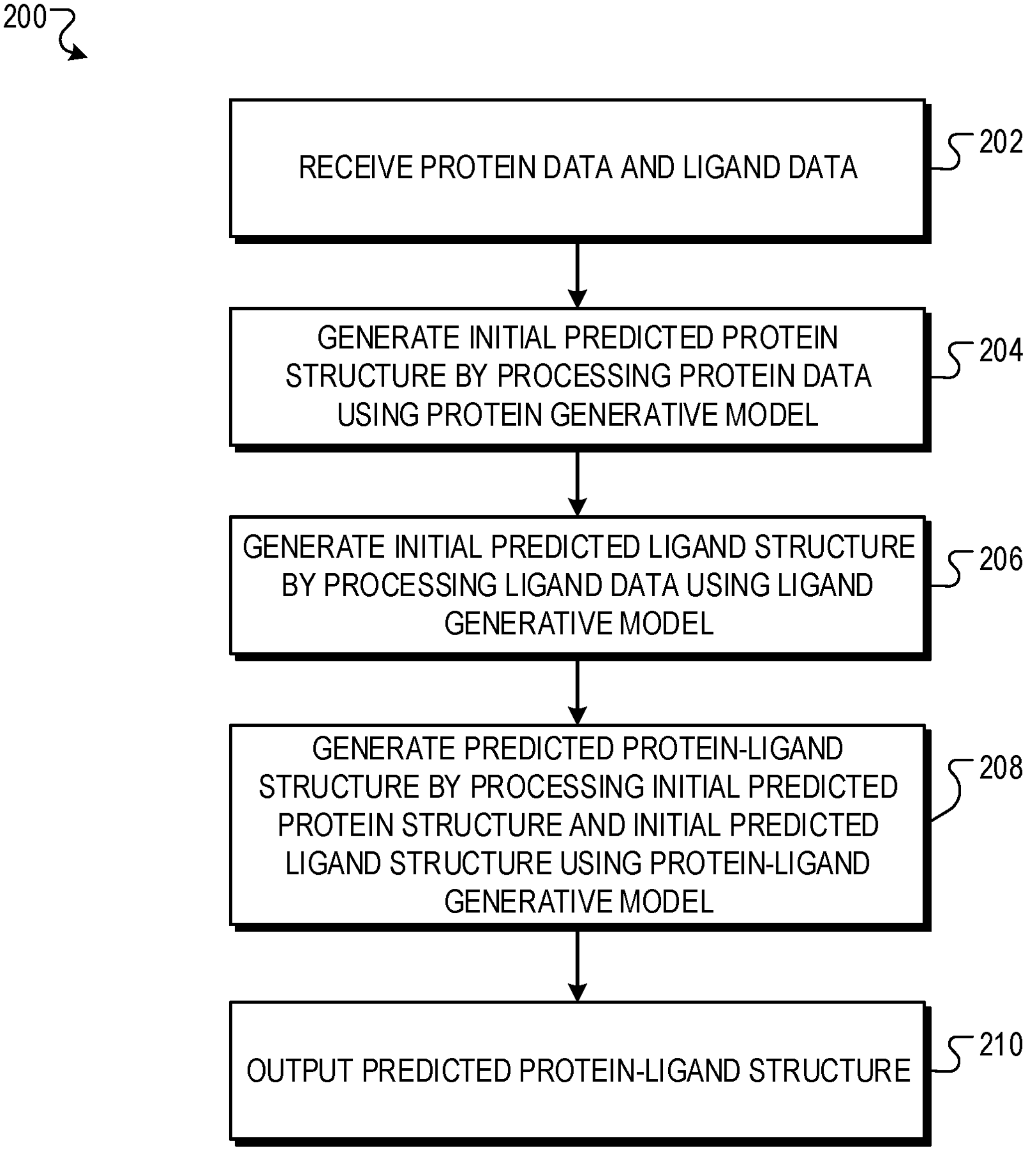
FIG. 2 is a flow diagram of an example process for generating a predicted 3D structure for a protein-ligand complex using a modular structure prediction system.

FIG. 2 is a flow diagram of an example process for generating a predicted 3D structure for a protein-ligand complex using a modular structure prediction system. For convenience, the process 200 will be described as being performed by a system of one or more computers located in one or more locations. For example, a modular structure prediction system, e.g., the modular structure prediction system 100 of FIG. 1, appropriately programmed in accordance with this specification, can perform the process 200.

The system can receive protein data characterizing a protein and ligand data characterizing a ligand (step 202). As described above the ligand data can characterize any of a variety of ligands. For example, the ligand data can characterize a small molecule ligand (e.g., a ligand that is a non-polymer organic molecule with a low molecular weight). As another example, the ligand data can characterize a poly-peptide ligand that is, itself, a protein. As another example, the ligand data can characterize a nucleic acid (e.g., a ribonucleic acid (RNA), a deoxyribonucleic acid (DNA), and so on).

In general, the protein data and the ligand data can specify chemical compositions of the protein and the ligand, respectively. As an example, the protein data and the ligand data can include data specifying atoms, charges on atoms, bonds, functional groups, amino acids, branches (e.g., from a molecule main chain), ring structures, and so forth within the protein and the ligand. For example, the protein data and the ligand data can include, e.g., Simplified Molecular Input Line Entry System (SMILES) formatted data, International Chemical Identifier (InChI) formatted data, and so on specifying some or all of the protein, the ligand, or both (e.g., specifying compositions molecular components of the protein, the ligand, or both, such as amino acid residues, nucleotides, etc.).

The protein data can specify the chemical composition of the protein by specifying an amino acid sequence for the protein. The amino acid sequence for the protein can specify an identity and an ordering for each of a plurality of amino acid residues within the protein. In some implementations, the protein data can include a multiple sequence alignment (MSA) for the protein characterizing an alignment of a plurality of amino acid sequences associated with the protein. In some implementations, the protein data can include data characterizing known 3D structures (e.g., as determined by physical experiments) for one or more template amino acid sequences.

Similarly, when the ligand is a protein itself, the ligand data can specify the chemical composition of the ligand by specifying an amino acid sequence for the ligand. When the ligand is a protein, the ligand data can include, e.g., an MSA for the ligand characterizing an alignment of a plurality of amino acid sequences associated with the ligand, data characterizing known 3D structures for one or more template amino acid sequences for the ligand, and so on.

When the ligand is a nucleic acid, the ligand data can specify the chemical composition of the ligand by specifying a nucleotide sequence for the ligand. The nucleotide sequence for the ligand can specify an identity and an ordering for each of a plurality of nucleotides within the ligand.

In some implementations, the protein data can include data characterizing an initial or estimated 3D structure for the protein. The initial or estimated 3D structure of the protein can be determined by any of a variety of means, such as by physical experiment (e.g., x-ray crystallography), by computational simulation (e.g., by molecular dynamics simulations, quantum mechanical simulations, etc.), and so on. As an example, the initial or estimated 3D structure of the protein can be an unfolded or a partially folded structure for the protein. When the protein data characterizes an initial or estimated 3D structure for the protein, the protein data can specify the chemical composition and 3D structure for the protein by specifying a chemical element and a spatial position for each atom of the protein.

Similarly, in some implementations, the ligand data can include data characterizing an initial or estimated 3D structure for the ligand (e.g., as determined by physical experiment, computational simulation, etc.).

The system can receive the protein data and the ligand data by any appropriate means. As an example, the system can receive the protein data, the ligand data, or both from a user (e.g., by way of a user interface, an application programming interface (API), etc.). As another example, the system can receive the protein data, the ligand data, or both from another system (e.g., an upstream system).

The system can generate data characterizing an initial predicted 3D structure for the protein by processing the protein data using a protein generative model (step 204). The initial predicted 3D structure for the protein can characterize a predicted unbound structure for the protein (e.g., a predicted structure for the protein in isolation from the ligand).

In general, the data characterizing the initial predicted 3D structure for the protein can characterize spatial positions for each atom within the protein. For example, the protein generative model can generate data that directly specifies the initial predicted 3D structure for the protein (e.g., by specifying positions of atoms within the predicted 3D structure, structure parameters of the initial predicted 3D structure such as torsion angles and bond lengths, positions and orientations of groups of atoms within the initial predicted 3D structure, and so on).

As another example, the protein generative model can generate a latent representation of the initial predicted 3D structure for the protein. The latent representation can include a plurality of embeddings, with each embedding representing, e.g., a respective atom of the protein, a respective group of atoms of the protein, and so on. The latent representation can be an output from an intermediate layer of the protein generative model (e.g., an output from any hidden layer of the protein generative model that is between an input layer of the protein generative model and an output generative model in a directed graph of layers of the protein generative model). The latent representation of the initial predicted 3D structure for the protein can be processed (e.g., by one or more output layers of the protein generative model, by another neural network, etc.) to determine the spatial positions for each atom within the protein.

The protein generative model can have any appropriate architecture for processing the protein data to generate the initial predicted 3D structure for the protein. The protein generative model can be, e.g., a generative adversarial network, a denoising diffusion model, a flow-based generative model, and so on. For example, the protein generative model can have a generative architecture as described by, e.g., Abramson et al. in "Accurate Structure Prediction of Biomolecular Interactions with AlphaFold 3", Watson et al. in "De Novo Design of Protein Structure and Function with RFdiffusion", and so on. In particular, the protein generative model can be a structure prediction generative model configured (e.g., trained) to generate predicted 3D structures for proteins by processing corresponding protein data for the proteins, as described in more detail below with reference to FIGS. 3-9. In particular, the system can generate the initial predicted 3D structure for the protein using the protein generative model following process 500 of FIG. 5. The protein generative model can be trained (e.g., pre-trained) following process 700 of FIG. 7 using training data for the protein generative model that includes example protein data characterizing example proteins and target predicted structures for the example proteins.

The system can generate data characterizing an initial predicted 3D structure for the ligand by processing the ligand data using a ligand generative model (step 206). The initial predicted 3D structure for the ligand can characterize a predicted unbound structure for the ligand (e.g., a predicted structure for the ligand in isolation from the protein).

In general, the data characterizing the initial predicted 3D structure for the ligand can characterize spatial positions for each atom within the ligand. For example, the ligand generative model can generate data that directly specifies the initial predicted 3D structure for the ligand (e.g., by specifying positions of atoms within the predicted 3D structure, structure parameters of the initial predicted 3D structure such as torsion angles and bond lengths, positions and orientations of groups of atoms within the initial predicted 3D structure, and so on).

As another example, the ligand generative model can generate a latent representation of the initial predicted 3D structure for the ligand. The latent representation can include a plurality of embeddings, with each embedding representing, e.g., a respective atom of the ligand, a respective group of atoms of the ligand, and so on. The latent representation can be an output from an intermediate layer of the ligand generative model (e.g., an output from any hidden layer of the ligand generative model that is between an input layer of the ligand generative model and an output generative model in a directed graph of layers of the ligand generative model). The latent representation of the initial predicted 3D structure for the ligand can be processed (e.g., by one or more output layers of the ligand generative model, by another neural network, etc.) to determine the spatial positions for each atom within the ligand.

The ligand generative model can have any appropriate architecture for processing the ligand data to generate the initial predicted 3D structure for the ligand. The ligand generative model can be, e.g., a generative adversarial network, a denoising diffusion model, a flow-based generative model, and so on. For example, the ligand generative model can have a generative architecture as described by, e.g., Abramson et al. in "Accurate Structure Prediction of Biomolecular Interactions with AlphaFold 3", Watson et al. in "De Novo Design of Protein Structure and Function with RFdiffusion", and so on. In particular, the ligand generative model can be a structure prediction generative model configured (e.g., trained) to generate predicted 3D structures for ligands by processing corresponding ligand data for the ligands, as described in more detail below with reference to FIGS. 3-9. In particular, the system can generate the initial predicted 3D structure for the ligand using the ligand generative model following process 500 of FIG. 5. The ligand generative model can be trained (e.g., pre-trained) following process 700 of FIG. 7 using training data for the ligand generative model that includes example ligand data characterizing example ligands and target predicted structures for the example ligands.

The system can generate a predicted 3D structure of a protein-ligand complex including the protein and the ligand by processing the initial predicted 3D structure for the protein and the initial predicted 3D structure for the ligand using a protein-ligand generative model (step 208). The predicted 3D structure of the protein-ligand complex can characterize predicted bound structures for the ligand and the protein of the protein-ligand complex (e.g., predicted joint structures for the protein and the ligand when the protein and ligand are bound with one another).

The protein-ligand generative model can have any appropriate architecture for processing the initial predicted 3D structures of the protein and the ligand to generate the predicted 3D structure for the protein-ligand complex. The protein-ligand generative model can be, e.g., a generative adversarial network, a denoising diffusion model, a flow-based generative model, and so on. For example, the protein-ligand generative model can have a generative architecture as described by, e.g., Abramson et al. in "Accurate Structure Prediction of Biomolecular Interactions with AlphaFold 3", Watson et al. in "De Novo Design of Protein Structure and Function with RFdiffusion", and so on. In particular, the protein-ligand generative model can be a structure prediction generative model configured (e.g., trained) to generate predicted 3D structures for protein-ligand complexes by processing data characterizing initial (e.g., unbound) structures for the proteins and ligands of the protein-ligand complexes, as described in more detail below with reference to FIGS. 3-7. In particular, the system can generate the predicted 3D structure for the protein-ligand complex using the protein-ligand generative model following process 500 of FIG. 5. The protein-ligand generative model can be trained (e.g., pre-trained) following process 700 of FIG. 7 using training data for the protein-ligand generative model that includes example initial (e.g., unbound) structures for proteins and ligands of example protein-ligand complexes and target predicted structures for the example protein-ligand complexes.

In some implementations, in addition to processing the processing the initial predicted 3D structure for the protein and the initial predicted 3D structure for the ligand, the protein-ligand generative model can also process the protein data and the ligand data specifying the chemical compositions of the protein and the ligand as part of generating the predicted 3D structure of the protein-ligand complex.

In some implementations, the protein-ligand generative model can be jointly trained (e.g., fine-tuned) with the protein generative model and the ligand generative model to generate predicted 3D structures for example protein-ligand complexes by processing initial protein and ligand structures generated by the protein generative model and the ligand generative model, as described in more detail below with reference to FIG. 10.

The system can output the predicted 3D structure of the protein-ligand complex including the protein and the ligand (step 210). The system can output the predicted 3D structure of the protein-ligand complex for use in any of a variety of down-stream tasks. As an example, as described in more detail below with reference to FIG. 11 and FIG. 12, the predicted 3D structure of the protein-ligand complex can be processed as part of screening a set of candidate ligands or a set of candidate proteins, e.g., for physical synthesis, to perform further validation, and so on.

Figure 3:
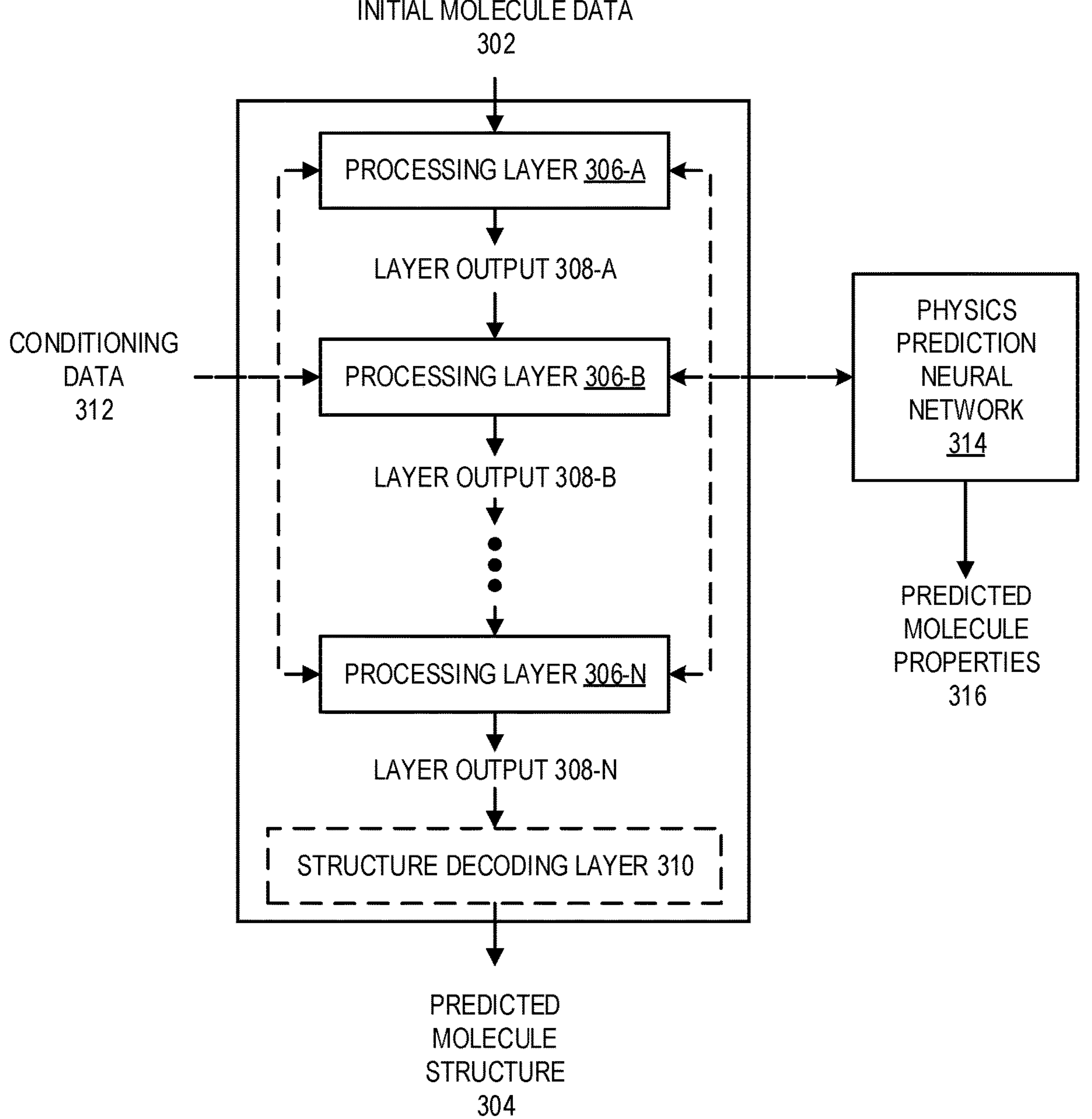
FIG. 3 is a block diagram of an example structure prediction generative model.

FIG. 3 is a block diagram of an example structure prediction generative model 300. The structure prediction generative model 300 is an example of a system implemented as computer programs on one or more computers in one or more locations in which the systems, components, and techniques described below are implemented.

The structure prediction generative model 300 can process initial molecule data 302 for a molecule system to generate a predicted 3D structure 304 for the molecule system. The molecule system can be a system of atoms (e.g., an atomic system) characterizing one or more molecules, e.g., a protein, a ligand, a nucleic acid, a molecule complex such as a protein-ligand complex, and so on. The initial molecule data 302 can characterize a noisy 3D structure for the molecule system specifying noisy initial positions for each atom of the molecule system. As part of processing the initial molecule data 302, the structure prediction generative model 300 can transform (e.g., denoise, diffuse, etc.) the noisy 3D structure for the molecule system specified by the initial molecule data 302 to generate the predicted 3D structure 304 for the molecule system.

As described above, the structure prediction generative model 300 can be configured to generate predicted 3D structures for any of a variety of molecule systems. For example, the structure prediction generative model 300 can be a protein generative model configured to process protein data characterizing a protein to generate a predicted 3D structure 304 for the protein. As another example, the structure prediction generative model 300 can be a ligand generative model configured to process initial molecule data 302 characterizing a ligand to generate a predicted 3D structure 304 for the ligand. As another example, the structure prediction generative model 300 can be a protein-ligand generative model configured to process initial molecule data 302 characterizing a protein and a ligand to generate a predicted 3D structure 304 for a protein-ligand complex that includes the protein and the ligand.

In general, the structure prediction generative model 300 can receive data specifying a chemical composition of the molecule system and can generate the initial molecule data 302 based on the specified chemical composition of the molecule system. For example, structure prediction generative model 300 can generate the initial molecule data 302 by processing data specifying atoms, charges on atoms, bonds, functional groups, amino acids, branches (e.g., from a molecule main chain), ring structures, and so forth within the molecule system. As a further example, the structure prediction generative model 300 can generate the initial molecule data 302 by processing, e.g., Simplified Molecular Input Line Entry System (SMILES) formatted data, International Chemical Identifier (InChI) formatted data, and so on specifying a chemical structure for portions of or all of the molecule system.

As another example, the structure prediction generative model 300 can generate the initial molecule data 302 by processing data specifying one or more amino acid sequence for the molecule system. Each amino acid sequence for the molecule system can specify an identity and an ordering for each of a plurality of amino acid residues within a molecule (e.g., a protein, a ligand, etc.) of the molecule system.

In some implementations, the structure prediction generative model 300 can receive and process data characterizing initial or estimated 3D structures for one or more molecules of the molecule system as part of generating the initial molecule data 302. The initial or estimated 3D structures of the one or more molecules can be determined by any of a variety of means, such as by physical experiment (e.g., x-ray crystallography), by computational simulation (e.g., by molecular dynamics simulations, quantum mechanical simulations, etc.), and so on. As an example, the initial or estimated 3D-structure of a protein can be an unfolded or a partially folded structure for the protein. As another example, when the structure prediction generative model 300 is a protein-ligand generative model, the model 300 can generate the initial molecule data 302 for a protein-ligand complex by processing initial 3D structures for the ligand and the protein (e.g., initial predicted 3D structures for the ligand and the protein as generated by a ligand generative model and a protein generative model). The data characterizing the initial or estimated 3D structures for the one or more molecules can specify chemical compositions and 3D structures for the one or more molecules by specifying a chemical element and an initial spatial position for each atom of the one or more molecules.

The structure prediction generative model 300 can generate the initial molecule data 302 using the received data characterizing the chemical composition of the molecule system by any of a variety of methods. As an example, the model 300 can sample an initial noisy spatial position for each atom of the molecule system from a distribution of noisy spatial positions for the atom. As another example, when the model receives data specifying initial or estimated 3D structures for one or more molecules of the molecule system, the model 300 can generate the initial molecule data 302 by determining the initial noisy spatial position for each atom of the molecule system as specified by the initial or estimated 3D structures for the one or more molecules of the molecule system.

The structure prediction generative model 300 can process the initial molecule data 302 over a sequence of processing iterations to generate the predicted molecule structure 304. For example, as illustrated in FIG. 3, the structure prediction generative model can process the initial molecule data 308 over a sequence of processing iterations using processing layers 306-A through 306-N. At each processing iteration, a respective one of the processing layers 306-A through 306-N for the processing iteration can process a respective layer input to generate a respective one of layer outputs 308-A through 308-N. The processing layer 306-A can (e.g., during a first processing iteration) process the initial molecule data 302 to generate the layer output 308-A. Each of the processing layers 306-B through 306-N can (e.g., at each subsequent processing iteration) process the layer output from a previous processing iteration to generate the respective layer outputs 308-B through 308-N. The final layer output 308-N (e.g., the layer output generated during the final processing iteration) can characterize the predicted model structure 304 for the molecule system.

In some implementations, the processing layers 306-A through 306-N can be a same, shared processing layer for each of the processing iterations and each of the layer outputs 308-A through 308-N can be generated following a same processing operation to be an incremental update of a predicted 3D structure for the molecule system. As an example, the structure prediction generative model 300 can be a denoising neural network configured to generate the predicted molecule structure 304 over a sequence of denoising iterations. As a further example, each of the processing layers 306-A through 306-N can be a same, shared denoising network layer configured to sample the layer outputs 308-A through 308-N from distributions determined by processing the respective layer inputs (e.g., using a diffusion sampling technique). As another example, the structure prediction generative model 300 can be a flow based generative model configured to generate the predicted molecule structure 304 in accordance with a set of transformation differential equations characterizing a transformation from a distribution (e.g., a noise distribution) for the initial molecule data 302 to a distribution for the predicted molecule structure 304. When the structure prediction generative model 300 is a flow based generative model, each of the processing layers 306-A through 306-N can be a same, shared processing network layer configured to generate the layer outputs 308-A through 308-N in accordance with the set of transformation differential equations determined for the corresponding layer input (e.g., by numerically integrating the set of transformation differential equations for the corresponding layer input).

The initial molecule structure 304 can represent (e.g., encode) a 3D structure for the molecule system using any appropriate scheme for encoding the positions of atoms within the molecule system and the processing layers 306-A through 306-N can have any appropriate neural network architectures suitable for processing (e.g., denoising, transforming, etc.) layer inputs representing respective 3D structures for the molecule system. The layer outputs 308-A through 308-N can represent (e.g., encode) respective 3D structures for the molecule system using the same encoding scheme as used by the initial molecule structure 304. By stochastically generating the predicted molecule structure 304 (e.g., by sampling the initial molecule data 302 from an initial distribution, by adding and processing sampled noise using the processing layers 306-A through 306-N, etc.), the structure prediction generative model 300 can therefore sample the predicted molecule structure 304 from a distribution over a space of possible 3D structures for the molecule system.

In general, the initial molecule structure 304 can include a plurality of numerical features that specify 3D spatial positions for each atom within the molecule system. For example, the initial molecule structure 304 can be a vector of numerical values that specifies 3D spatial positions for each atom within the molecule system. As another example, the initial molecule structure 304 can include a plurality of vectors of numerical values, each representing a respective atom or group of atoms (e.g., a respective amino acid residue, functional group, etc.) within the molecule system. For example, the initial molecule structure 304 can be a sequence of tokens, with each token representing a respective atom or group of atoms (e.g., a respective amino acid residue, functional group, etc.). As another example, the initial molecule structure 304 can be a graph representation of the molecule system that includes a plurality of graph nodes that each represent a respective atom or group of atoms (e.g., a respective amino acid residue, functional group, etc.).

When the initial molecule structure 304 includes embeddings (e.g., feature vectors, tokens, graph node embeddings, etc.) representing respective groups of atoms (e.g., respective amino acid residues, functional groups, etc.) within the molecule system, the initial molecule structure 304 can specify positions and orientations (e.g., rotations) of each of the groups of atoms within the molecule system. In particular, in some implementations, the initial molecule structure 304 can specify relative rotations between groups of atoms within the molecule system using torsion angles between the groups of atoms, as described in more detail below with reference to FIG. 4.

The spatial positions of each atom within a group of atoms (e.g., respective amino acid residues, functional groups, etc.) can be determined by the embedding for the group of atoms within the initial molecule structure 304 (and, when applicable, any numerical features of the initial molecule structure 304 characterizing orientations of the group of atoms relative to other groups of atoms within the molecule system). As an example, the position of each atom within the group of atoms can be predefined and fixed and the position of each atom within the molecule system can be determined based on (i) the predefined location of the atom within the group of atoms and (ii) the location and orientation of the group of atoms specified by the embedding for the group of atoms. As another example, the embedding of the group of atoms can include numerical features specifying the position of each atom within the group of atoms and the position of each atom within the molecule system can be determined based on (i) the location of the atom within the group of atoms and (ii) the location and orientation of the group of atoms (e.g., both specified by the embedding for the group of atoms).

When the initial molecule structure 304 is a latent representation of a 3D structure for the molecule system, the structure prediction generative model 300 can include a decoder neural network 310 configured to determine the 3D positions of atoms within the molecule system specified by latent representations for the molecule system. For example, when the final layer output 308-N uses a latent encoding scheme to represent the predicted molecule structure 304 for the molecule system, the decoder neural network 310 can process the final layer output 308-N to generate the predicted molecule structure 304 for the molecule system.

As described above, the processing layers 306-A through 306-N can have any appropriate neural network architectures suitable for processing (e.g., denoising, transforming, etc.) layer inputs that include embeddings (e.g., feature vectors, tokens, graph nodes, etc.) representing atoms or groups of atoms within the molecule system. For example, when the initial molecule data 302 and the layer outputs. 308-A through 308-N include sequences of tokens, the processing layers 306-A through 306-N can include attention neural network layers configured to generate respective output token sequences by performing respective attention operations. As another example, when the initial molecule data 302 and the layer outputs 308-A through 308-N include respective graphs representing 3D structures for the molecule system, the processing layers 306-A through 306-N can include graph processing layers (e.g., message passing layers) configured to generate respective output graphs representing the molecule system by performing respective graph processing operations (e.g., using a message passing process).

In some implementations, the structure prediction model 300 can receive conditioning data 312 and can conditionally process the initial molecule data 302 using the conditioning data 312 to generate the predicted molecule structure 304 for the molecule system. The conditioning data 312 can include any appropriate data for conditional molecular structure generation. As an example, the conditioning data 312 can specify physical conditions (e.g., temperatures, pressures, salinities, acidities, etc.) for the molecule system and the model 300 can generate the predicted molecule structure 304 for the molecule system under the specified physical conditions. As another example, when the structure prediction model 300 is a protein-ligand generative model, the conditioning data 312 can include initial (e.g., unbound) predicted structures for a protein and a ligand and the model 300 can generate the predicted molecule structure 304 for a protein-ligand complex of the protein and the ligand as conditioned on the initial predicted structures for a protein and a ligand. In some implementations, when the structure prediction model 300 is a protein-ligand generative model, the conditioning data 312 can include latent representations of the initial predicted structures for the protein and the ligand (e.g., latent representations as an output from intermediate layers of a protein generative model and a ligand generative model, respectively, that can be processed to determine spatial positions for each atom within the protein and the ligand) and the model 300 can generate the predicted molecule structure 304 for a protein-ligand complex of the protein and the ligand as conditioned on the initial predicted (unbound) structures for a protein and a ligand.

When the structure prediction generative model 300 receives conditioning data 312, the processing layers 306-A through 306-N can each be configured to conditionally process respective layer inputs using the conditioning data 312 to generate the layer outputs 308-A through 308-N. As an example, the processing layers 306-A through 306-N can be configured to process respective layer inputs that include the conditioning data 312 to generate the layer outputs 308-A through 308-N. As another example, when the processing layers 306-A through 306-N include attention neural network layers configured to generate output token sequences by performing respective attention operations, the processing layers 306-A through 306-N can include one or more cross-attention layers configured to perform cross-attention operations between input token sequences and conditioning token sequences representing the conditioning data 312. As another example, the processing layers 306-A through 306-N can process the conditioning data 312 to determine respective adjustments to the respective layer outputs using a ControlNet neural network, as described by Zhang et al. in "Adding Conditional Control to Text-to-Image Diffusion Models".

In some implementations, as part of generating the layer outputs 308-A through 308-N, the processing layers 306-A through 306-N can be configured to determine gradients of energies of the molecule structures represented by the respective layer inputs. In particular, the processing layers 306-A through 306-N can be configured to determine the gradients of the energies of the molecule structures using predicted molecule properties (e.g., predicted energies, atomic forces, electron densities, etc.) generated by a physics prediction neural network 314. The physics prediction neural network 314 can be configured (e.g., trained) to process data characterizing molecule structures represented by the respective layer inputs of the processing layers 306-A through 306-N to generate predicted molecule properties for the molecule structures. In some implementations, as described in more detail with reference to FIG. 6A and FIG. 6B, the structure prediction generative model 300 can be jointly trained with the physics prediction neural network 314.

In some implementations, the structure prediction generative model 300 can share network parameters with the physics prediction neural network 314. For example, the structure prediction generative model 300 can include any combination of network layers, blocks, and so on of the physics prediction neural network 314. In particular, each of the processing layers 306-A through 306-N can share network parameters with the physics prediction neural network 314. For example, each of the processing layers 306-A through 306-N can include any combination of network layers, blocks, and so on of the physics prediction neural network 314. As described in more detail below with reference to FIG. 6B, sharing parameters with the physics prediction neural network 314 enables portions of the structure prediction generative model 300 to be trained as part of training the physics prediction neural network 314.

As described in more detail below with reference to FIG. 5, the processing layers 306-A through 306-N can generate the layer outputs 308-A through 308-N using the determined gradients so as to perform a gradient descent of the energy of the molecule structure over the sequence of processing iterations.

Processing the initial molecule data 302 to generate the predicted molecule structure 304 using the structure prediction generative model 300 is described in more detail below with reference to FIG. 5.

In general, the structure prediction generative model 300 can be trained (e.g., pre-trained, fine-tuned, etc.) to optimize an objective function for the model 300 using a set of training data that includes example molecule systems and target 3D structures for the example molecule systems. An example process for training the structure prediction generative model 300 is described in more detail below with reference to FIG. 7.

The structure prediction generative model 300 can be jointly trained alongside other structure prediction generative models (e.g., to process predicted molecule structures generated by other structure prediction generative models and/or to generate predicted molecule structures 304 to be processed by other structure prediction generative models). An example process for jointly training multiple structure prediction generative models is described in more detail below with reference to FIG. 10.

The predicted 3D structure 304 for the molecule system can be used as part of performing any of a variety of down-stream tasks. As one example, the predicted 3D structure 304 for the molecule system can be processed by another structure prediction generative model to generate a predicted 3D structure for a molecule complex that includes the molecule system. As a further example, the molecule system can be a protein or a ligand included within a protein-complex and the predicted 3D structure 304 for the molecule system can be processed by a structure prediction generative model for protein-ligand complexes to generate a predicted 3D structure for the protein-ligand complex that includes the molecule system.

As another example, the predicted 3D structure 304 for the molecule system can be processed to determine predicted molecule properties (e.g., a binding affinity, a free energy, atomic forces, an electron density, etc.) for the molecule system. For example, the predicted molecule properties for the molecule system can be determined by performing a computational simulation (e.g., a molecular dynamics simulation, a quantum mechanical simulation, etc.) of the predicted 3D structure 304 for the molecule system. As another example, the predicted molecule properties for the molecule system can be determined by processing the predicted 3D structure 304 using a molecule property prediction neural network configured (e.g., trained) to generate predicted molecule properties by processing 3D structures for molecule systems.

As described above, the initial molecule structure 304 can specify relative rotations between groups of atoms within the molecule system using torsion angles between the groups of atoms. An example of a torsion angle that can be specified by the initial molecule structure 304 is described next.

Figure 4:
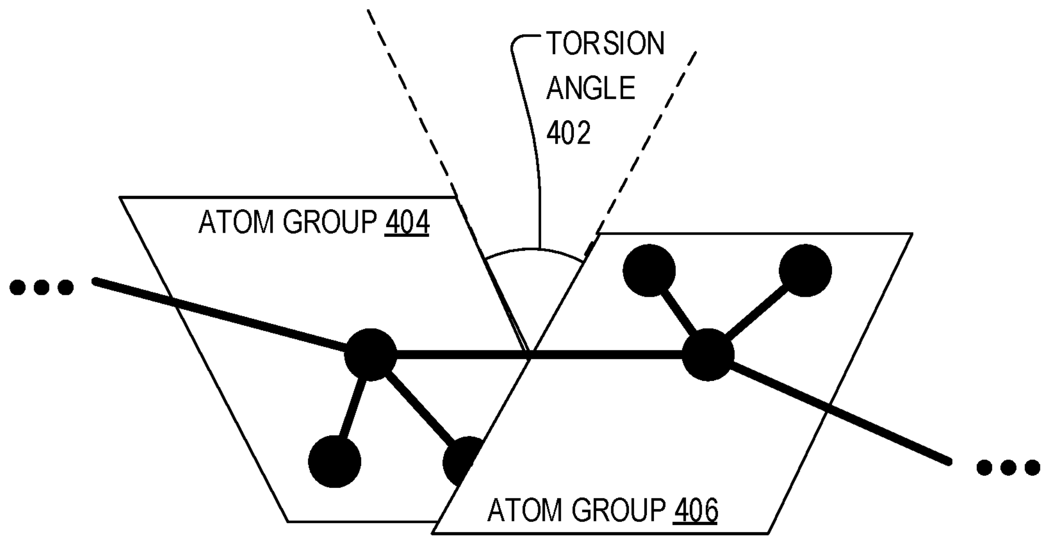
FIG. 4 illustrates a torsion angle between two groups of atoms for a molecule system.

FIG. 4 illustrates a torsion angle between two groups of atoms for a molecule system.

As described above with reference to FIG. 3, a structure prediction generative model can process an initial, noisy molecular structure for a molecule system to generate a predicted molecule structure for the molecule system. In general, the structure prediction generative model can process and generate embeddings of the molecule structure that specify 3D spatial locations for each atom within the molecule system. In particular, the structure prediction generative model can process and generate multiple embeddings (e.g., feature vectors, tokens, graph nodes, etc.) for the molecule system, with each embedding characterizing a position and orientation of a respective group of atoms (e.g., a respective amino acid, functional group, etc.) within the molecule system.

As an example, the structure prediction generative model can process and generate respective embeddings for atom groups 404 and 406 of FIG. 4. The structure prediction generative model can also process and generate a torsion angle 402 between the atom groups 404 and 406 within the molecule that specifies a relative orientation between the atom groups 404 and 406. The torsion angle 402 specifies an angle between a plane for the atom group 404 and a plane for the atom group 406. In particular, when atoms of the atom groups 404 and 406 share a chemical bond, the torsion angle 402 can specify an angle between the planes for the atom groups 404 and 406 and within a plane normal to the chemical bond between the atom groups 404 and 406.

The structure prediction generative model can process and generate a plurality of torsion angles for a molecule system. For example, the structure prediction generative model can process and generate side-chain torsion angles for a protein (e.g., torsion angles between side-chain atom groups and back-bone atom groups for the protein), back-bone torsion angles for a protein (e.g., torsion angles between different back-bone atom groups for the protein), and so on.

Figure 5:
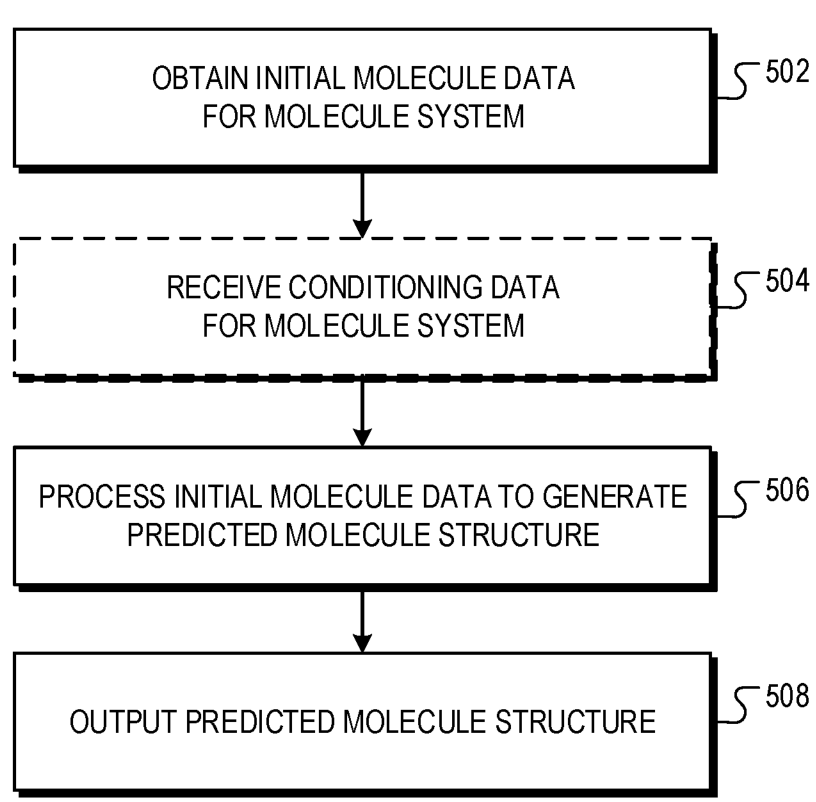
FIG. 5 is a flow diagram of an example process for generating a predicted 3D structure for a molecule system using a structure prediction generative model.

FIG. 5 is a flow diagram of an example process for generating a predicted 3D structure for a molecule system using a structure prediction generative model. For convenience, the process 500 will be described as being performed by a system of one or more computers located in one or more locations. For example, a structure prediction generative model, e.g., the structure prediction generative model 300 of FIG. 3, appropriately programmed in accordance with this specification, can perform the process 500.

The system can obtain initial molecule data for the molecule system (step 502). The molecule system can be, e.g., a protein, a ligand, a protein-ligand complex, and so on. In general, the system can receive data specifying a chemical composition of the molecule system and can generate the initial molecule data based on the specified chemical composition of the molecule system. For example, the system can generate the initial molecule data by receiving and processing data specifying atoms, charges on atoms, bonds, functional groups, amino acids, branches (e.g., from a molecule main chain), ring structures, and so forth within the molecule system. As a further example, the system can generate the initial molecule data by receiving and processing, e.g., Simplified Molecular Input Line Entry System (SMILES) formatted data, International Chemical Identifier (InChI) formatted data, and so on specifying a chemical structure for portions of or all of the molecule system.

As another example, the system can generate the initial molecule data by receiving and processing data specifying one or more amino acid sequences for one or more molecules of the molecule system. Each amino acid sequence for the molecule system can specify an identity and an ordering for each of a plurality of amino acid residues within a molecule of the molecule system.

In some implementations, the system can receive and process data characterizing initial or estimated 3D structures for one or more molecules of the molecule system as part of generating the initial molecule data. The initial or estimated 3D structures of the one or more molecules of the molecule system can be determined by any of a variety of means, such as by physical experiment (e.g., x-ray crystallography), by computational simulation (e.g., by molecular dynamics simulations, quantum mechanical simulations, etc.), and so on. As an example, the initial or estimated 3D structure of a protein can be an unfolded or a partially folded structure for the protein. As another example, when the system is configured to generate predicted molecule structures for protein-ligand complexes, the system can generate the initial molecule data for a protein-ligand complex by receiving and processing initial 3D structures for a ligand and a protein of the protein-ligand complex (e.g., initial predicted 3D structures for the ligand and the protein as generated by a ligand generative model and a protein generative model). The data characterizing the initial or estimated 3D structures for one or more molecules of the molecule system can specify chemical compositions and 3D structures for the one or more molecules by specifying a chemical element and an initial spatial position for each atom of the one or more molecules.

The system can generate the initial molecule data using the received data characterizing the chemical composition of the molecule system by any of a variety of methods. As an example, the system can sample an initial noisy spatial position for each atom of the molecule system from a distribution of noisy spatial positions for the atom. As another example, when the system receives data specifying initial or estimated 3D structures for one or more molecules of the molecule system, the system can generate the initial molecule data by determining the initial noisy spatial position for each atom of the molecule system as specified by the initial or estimated 3D structures for the one or more molecules of the molecule system.

The initial molecule data can include a plurality of numerical features that specify 3D spatial positions for each atom within the molecule system. For example, the initial molecule data can be a vector of numerical values that specifies 3D spatial positions for each atom within the molecule system. As another example, the initial molecule data can include a plurality of vectors of numerical values, each representing a respective atom or group of atoms (e.g., a respective amino acid residue, functional group, etc.) within the molecule system. For example, the initial molecule data can be a sequence of tokens, with each token representing a respective atom or group of atoms (e.g., a respective amino acid residue, functional group, etc.): As another example, the initial molecule data can be a graph representation of the molecule that includes a plurality of graph nodes that each represent a respective atom or group of atoms (e.g., a respective amino acid residue, functional group, etc.).

When the initial molecule data includes embeddings (e.g., feature vectors, tokens, graph node embeddings, etc.) representing respective groups of atoms (e.g., respective amino acid residues, functional groups, etc.) within the molecule system, the initial molecule data can include structure parameters that specify positions and orientations (e.g., rotations) of each of the groups of atoms within the molecule system. In particular, in some implementations, the initial molecule data can include structure parameters specifying torsion angles (e.g., side chain torsion angles, back bone torsion angles, etc.) between groups of atoms of the molecule system. The spatial positions of each atom within a group of atoms can be determined by the embedding for the group of atoms within the initial molecule data (and, when applicable, structural parameters within the initial molecule data characterizing orientations of the group of atoms relative to other groups of atoms within the molecule system). As an example, the position of each atom within the group of atoms can be predefined and fixed and the position of each atom within the molecule system can be determined based on (i) the predefined location of the atom within the group of atoms and (ii) the location and orientation of the group of atoms specified by the embedding for the group of atoms. As another example, the embedding of the group of atoms can include numerical features (e.g., structure parameters) specifying the position of each atom within the group of atoms and the position of each atom within the molecule system can be determined based on (i) the location of the atom within the group of atoms and (ii) the location and orientation of the group of atoms (e.g., both specified by the embedding for the group of atoms).

In some implementations, the initial molecule data can be a latent representation of a 3D structure for the molecule system.

In some implementations, the system can receive conditioning data for the molecule system (step 504). The conditioning data can include any appropriate data for conditional molecular structure generation. As an example, the conditioning data can specify physical conditions (e.g., temperatures, pressures, salinities, acidities, etc.) for the molecule system. As another example, when the system is configured to generate predicted molecule structures for protein-ligand complexes, the conditioning data can include initial (e.g., unbound) predicted structures for a protein and a ligand of a protein-ligand complex.

The system can process the initial molecule data for the molecule system to generate a predicted 3D structure for the molecule (step 506). In particular, the system can process the initial molecule data over a sequence of processing iterations to generate the predicted 3D structure for the molecule system. For example, the system can perform a denoising process (e.g., a reverse diffusion process) to denoise the initial molecule data over a sequence of denoising iterations to generate the predicted 3D structure for the molecule system.

As an example, the system can include a denoising neural network configured to generate an updated predicted 3D structure for the molecule system for an i-th denoising iteration, $x_i$, by sampling $x_i$ using a diffusion sampling technique from a distribution, $p_\theta(x_i|x_{i-1})$, defined by the denoising neural network processing the predicted 3D structure for the molecule system for the previous denoising iteration, $x_{i-1}$. In particular, the denoising neural network can be configured to process the predicted 3D structure for the molecule system for the previous denoising iteration, $x_{i-1}$, to generate parameters defining the distribution $p_\theta(x_i|x_{i-1})$. The parameters of defining the distribution $p_\theta(x_i|x_{i-1})$ can be any of a variety of parameters for determining a likelihood of the updated predicted 3D structure, $x_i$, such as means, covariances, and so on for variables of the updated predicted 3D structure (e.g., updated atom positions, updated structure parameters, updated latent representation features, etc.). The denoising neural network can sample the updated predicted 3D structure, $x_i$, in accordance with the distribution $p_\theta(x_i|x_{i-1})$ as defined by the generated parameters.

For example, the denoising neural network can be configured to generate the updated predicted 3D structure for the molecule system for an i-th denoising iteration, $x_i$, by sampling $x_i$ following:

$$x_i \sim \mathcal{N}\left(\mu_\theta(x_{i-1}|y); \sum\nolimits_\theta(x_{i-1}|y)\right)$$

Where $x_{i-1}$ is the predicted 3D structure for the molecule system for the previous denoising iteration (e.g., with $x_0$ being the noisy, initial molecule structure), $\mu_\theta$ and $\Sigma_\theta$ are neural networks configured to predict means and covariances for the denoised predicted 3D structure for the molecule system at each iteration (e.g., as optionally conditioned on conditioning data y).

In some implementations, the denoising neural network can be configured to sample a correction value, $z_i$, for predicted 3D structure for the molecule system for the i-th denoising iteration. For example, the denoising neural network can be configured to sample the correction value, $z_i$, for predicted 3D structure for the molecule system for the i-th denoising iteration following:

$$z_i \sim \mathcal{N}\left(\mu_\theta(x_{i-1}|y); \sum\nolimits_\theta(x_{i-1}|y)\right)$$

After sampling the correction value, $z_i$, the denoising neural network can generate the updated predicted 3D structure for the molecule system for an i-th denoising iteration, $x_i$, as a linear combination of the correction value and the predicted 3D structure for the molecule system for the previous denoising iteration, following:

$$x_i = z_i + x_{i-1}$$

As another example, the system can include a flow-based model configured to generate an updated predicted 3D structure for the molecule for an i-th denoising iteration, $x_i$, using a set of differential equations following:

$$x_i = x_{i-1} + \int_{t_{i-1}}^{t_i} f_\theta(x(t), t)dt$$

Where $f_\theta(x(t),t)$ is configured to predict a rate of change of variables of the molecule structure with respect to a continuous parameter t, $$\frac{dx(t)}{dt},$$

that defines a continuous transformation of the predicted structure of the molecule system from an initial distribution (e.g., a noise distribution) to a distribution of predicted 3D structures. In particular, the rate of change of variables of the molecule structure with respect to the continuous parameter t, $$\frac{dx(t)}{dt},$$

can define the continuous transformation of the predicted structure of the molecule system by specifying denoising trajectories for each variable of the molecule structure from the predicted 3D structure for the molecule system for the previous denoising iteration, $x_{i-1}$, to the updated predicted 3D structure for the molecule for the i-th denoising iteration, $x_i$. The predicted 3D structure at each iteration can be associated with a respective value of the parameter t such that $x_i=x(t_i)$ and $x_{i-1}=x(t_{i-1})$.

The system can numerically integrate the differential equations defined by the flow-based model at each denoising iteration to generate the updated predicted 3D structure for the molecule system for the i-th denoising iteration, $x_i$. For example, the system can generate the updated predicted 3D structure for the molecule system for the i-th denoising iteration, $x_i$, following:

$$x_i = x_{i-1} + (t_i - t_{i-1})f_\theta(x_{i-1}, t)$$

The flow-based model can be configured to determine reverse rates of change, $$f_\theta^{-1}(x(t), t),$$

that can be used to continuously transform the updated predicted 3D structure for the molecule for the i-th denoising iteration, $x_i$, to obtain the predicted 3D structure for the molecule system for the previous denoising iteration, $x_{i-1}$, following:

$$x_{i-1} = x_i + \int_{t_i}^{t_{i-1}} f_\theta^{-1}(x(t), t)dt$$

As described in more detail below with reference to FIG. 7, the system can use the reverse rates of change, $$f_\theta^{-1}(x(t), t),$$

to determine a likelihood of the flow based generative model generating (e.g., sampling) particular denoised predicted 3D structures for the molecule.

In some implementations, the system can update the predicted 3D structure at each denoising iteration using gradients of an energy of the predicted 3D structure with respect to parameters of the predicted 3D structure (e.g., with respect to atom positions, structure parameters, latent representation features, etc.). In particular, the system can update the predicted 3D structure at each denoising iteration to perform, in part, a gradient descent of the energy of the predicted 3D structure.

For example, when the system includes a denoising neural network, the system can sample a denoising output for the i-th denoising iteration, $z_i$, following:

$$z_i \sim \mathcal{N}\left(\mu_\theta(x_{i-1} \mid y); \sum\nolimits_\theta(x_{i-1} \mid y)\right)$$

And can then generate the updated predicted 3D structure for the molecule system for the i-th denoising iteration, $x_i$, following:

$$x_i = x_{i-1} + z_i - \alpha\nabla_x U(x_{i-1})$$

Where $\nabla_x U(x_{i-1})$ is a gradient of the energy, $U(x_{i-1})$, for the predicted structure for the molecule system with respect to the parameters of the molecule structure predicted at the previous denoising iteration and where $\alpha$ is a scalar weight between the denoising output and the energy gradient.

As another example, when the system includes a flow-based model, the system can determine the updated predicted 3D structure for the molecule system for an i-th denoising iteration, $x_i$, following:

$$x_i = x_{i-1} - \alpha\nabla_x U(x_{i-1}) + \int_{t_{i-1}}^{t_i} f_\theta(x(t), t)dt$$

Where α is a scalar weight between the integration of the differential equations defined by the flow-model, $$\int_{t_{i-1}}^{t_i} f_\theta(x(t), t)dt,$$

and the energy gradient, $\nabla_x U(x_{i-1})$.

The system can determine the energy gradient, $\nabla_x U(x_{i-1})$, by any of a variety of means. As one example, at each denoising iteration, the system can use an energy function to determine the energy, $U(x_{i-1})$, for the predicted structure for the molecule system at the previous denoising iteration. The energy function can depend on bond lengths for each of a plurality of bonds within the predicted structure and the system can determine the energy for the predicted structure by determining the bond lengths of each of the plurality of bonds within the predicted structure. For example, for each of the plurality of bonds within the predicted structure, the energy function can associate a respective energy the bond (e.g., an energy of a spring having a predefined spring force that is extended to a length defined by the bond length for the bond from a predefined length at rest, such as an expected length of the bond). After determining the energy for the predicted structure using the energy function, the system can differentiate the determined energy with respect to the parameters of the molecule structure to determine the energy gradient, $\nabla_x U(x_{i-1})$.

As another example, the system can determine the energy gradient, $\nabla_x U(x_{i-1})$, using a physics prediction neural network (e.g., the physics prediction neural network 314 of FIG. 3). The physics prediction neural network can be configured to process a network input that characterizes an atomic system (e.g., a system that includes a plurality of atoms, such as a molecule system) to generate a network output that defines one or more predicted properties of the atomic system. As an example, the physics prediction neural network can be configured to generate predicted energies of atomic systems and the system can determine a gradient of a predicted energy for the molecule system as generated by the physics prediction system. As another example, the physics prediction neural network can be configured to generate, for each of a plurality of atoms in an atomic system, a predicted force vector defining a predicted force on the atom and the system can determine the energy gradient using predicted force vectors for atoms within the molecule system generated by the physics prediction neural network. As another example, the physics prediction neural network can be configured to generate a predicted electron density at 3D spatial coordinates in atomic systems (e.g., by processing inputs specifying particular 3D spatial coordinates and generating predicted electron densities at the specified 3D spatial coordinates) and the system can determine the energy gradient using a predicted electron density for the molecule system generated by the physics prediction neural network.

The system can output the generated predicted 3D structure for the molecule system (step 508). In particular, when the system updates the predicted 3D structure for the molecule system over a sequence of diffusion iterations, the system can output the predicted 3D structure for the molecule system generated at the final diffusion iteration as the output predicted 3D structure for the molecule system.

The predicted 3D structure for the molecule system can be used as part of performing any of a variety of down-stream tasks. As one example, the predicted 3D structure for the molecule system can be processed by another structure prediction generative model (e.g., a structure prediction generative model for molecule complexes that include multiple molecules) to generate a predicted 3D structure for a molecule complex that includes molecules of the molecule system. As a further example, when the molecule system is a protein or a ligand included, the predicted 3D structure for the molecule system can be processed by a structure prediction generative model for protein-ligand complexes to generate a predicted 3D structure for a protein-ligand complex that includes the molecule system.

As another example, the predicted 3D structure for the molecule system can be processed to determine predicted molecule properties (e.g., a binding affinity, a free energy, atomic forces, an electron density, etc.) for the molecule system. For example, the predicted molecule properties for the molecule system can be determined by performing a computational simulation (e.g., a molecular dynamics simulation, a quantum mechanical simulation, etc.) of the predicted 3D structure for the molecule system. As another example, the predicted molecule properties for the molecule system can be determined by processing the predicted 3D structure using a molecule property prediction neural network configured (e.g., trained) to generate predicted molecule properties by processing 3D structures for molecule systems.

Figure 6A:
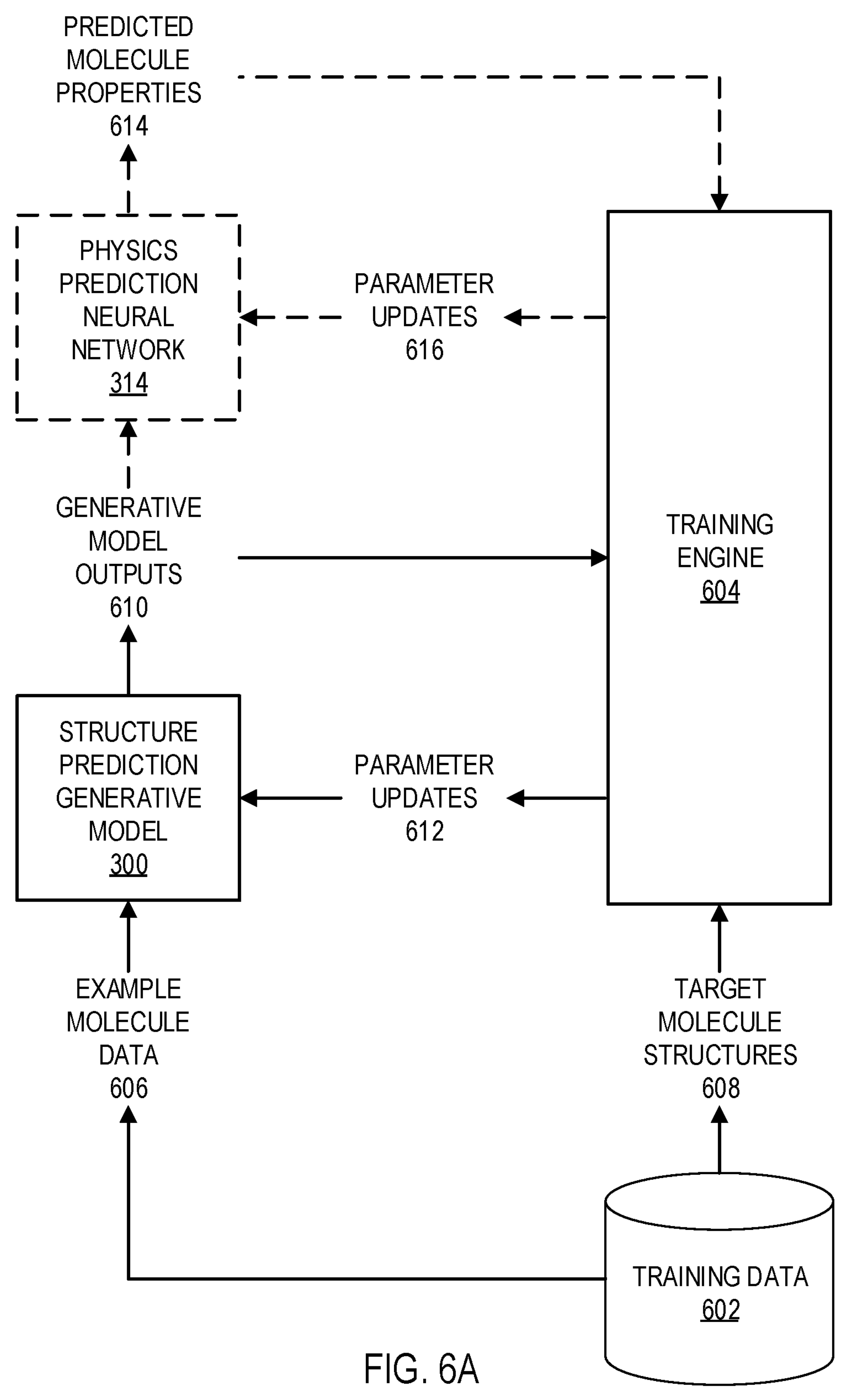
FIG. 6A illustrates training a structure prediction generative model using training data for the structure prediction generative model.

FIG. 6A illustrates training a structure prediction generative model 300 using training data 602 for the structure prediction generative model 300.

The training data 602 for the structure prediction generative model 300 can include example molecule data 606 characterizing a chemical composition for each of a plurality of example molecule systems and target molecule structures 608 for each of the example molecule systems.

The example molecule systems can be any appropriate type of molecule system for the structure prediction generative model 300. For example, the example molecule systems can be example proteins when the structure prediction model 300 is a protein generative model, example ligands when the structure prediction model 300 is a ligand generative model, example protein-ligand complexes when the structure prediction model 300 is a protein-ligand generative model, and so on.

The target molecule structures 608 for the example molecule systems can be obtained from any of a variety of sources. As an example, the training data 602 can include target molecule structures 608 for examples molecule systems as determined by physical experiment (e.g., as determined using x-ray crystallography of physical samples of the example molecule systems, cryo-electron microscopy (cryo-EM) of physical samples of the example molecule systems, and so on). As another example, the training data 602 can include target molecule structures 608 for examples molecule systems as determined by computational simulations (e.g., as determined using molecular dynamics simulations of the example molecule systems, quantum mechanical simulations of the example molecule systems, and so on). In particular, when the example molecule systems are protein-ligand complexes, the target molecule structures 608 for the example molecule systems can be determined using molecular docking computational simulations of the example molecule systems. Example techniques for performing molecular docking simulations include AutoDock 4, as described by Morris, Garrett M., et al. "AutoDock4 and AutoDockTools4: Automated docking with selective receptor flexibility." *Journal of Computational Chemistry* 30.16 (2009): 2785-2791; AutoDock Vina as described by Trott, Oleg, and Arthur J. Olson. "AutoDock Vina: improving the speed and accuracy of docking with a new scoring function, efficient optimization, and multithreading." *Journal of Computational Chemistry* 31.2 (2010): 455-461; GLIDE, as described by Friesner, Richard A., et al. "Glide: a new approach for rapid, accurate docking and scoring. 1. Method and assessment of docking accuracy." *Journal of Medicinal Chemistry* 47.7 (2004): 1739-1749; and MolDock, as described by Thomsen, René, and Mikael H. Christensen. "MolDock: a new technique for high-accuracy molecular docking." *Journal of Medicinal Chemistry* 49.11 (2006): 3315-3321.

In some implementations, the training data 602 can include target molecule structures for the example molecule systems obtained from different sources for pre-training or fine-tuning the structure prediction generative model 300. For example, the training data 602 can include target molecule structures 608 determined by computational simulation when pre-training the structure prediction generative model 300 and can include target molecule structures determined by physical experiment when fine-tuning the structure prediction generative model 300. Because computational simulation is less resource intensive compared to performing physical experimentation, using target molecule structures 608 determined by computational simulation can provide a larger and more easily obtained training set for pre-training the structure prediction generative model 300. Similarly, once the structure prediction model 300 has been pre-trained, using target molecule structures 608 determined by physical experiments can enable efficient fine-tuning of the structure prediction model 308 using a smaller set of experimentally determined target molecule structures 608 for the example molecule systems.

A training engine 604 can train the structure prediction generative model using the training data 602. In particular, the training engine 604 can determine parameter updates 612 for the structure prediction generative model 300 by processing generative model outputs 610 generated by structure prediction generative model 300 processing the example molecule data 606.

The generative model outputs 610 can include any of a variety of outputs generated by the structure prediction generative model 300 processing the example molecule data 606. For example, the generative model outputs 610 can include predicted molecule structures generated by the structure prediction generative model 300 for the example molecule systems. As another example, the generative model outputs 610 can include parameters defining conditional probability distribution of predicted molecule structures for the example molecule systems as conditioned on the example molecule data 606 for the example molecule systems. As another example, the generative model outputs 610 can include data characterizing conditional likelihoods of the structure prediction generative model 300 generating the target molecule structures 608 for the example molecule systems by processing the example molecule data 606 for the example molecule systems.

The training engine 604 can generate the parameter updates 612 by evaluating an objective function for the structure prediction generative model 300. In particular, the training engine 602 can generate the parameter updates 612 to optimize the objective function for the structure prediction generative model 300. The objective function for the structure prediction generative model 300 can include any of a variety of loss terms. For example, the objective function for the structure prediction generative model 300 can include a likelihood loss that encourages the structure prediction generative model 300 to generate the target molecule structures 608 for the example molecule systems by processing the example molecule data 606 for the example molecule systems. Examples of likelihood loss functions that can be included within the objective function for the structure prediction generative model 300 are described by Abramson et al. in "Accurate Structure Prediction of Biomolecular Interactions with AlphaFold 3" and by Watson et al. in "De Novo Design of Protein Structure and Function with RFdiffusion". As another example, as described in more detail below with reference to FIG. 8, the objective function for the structure prediction generative model 300 can include an alignment loss that encourages the structure prediction generative model 300 to generate physically plausible predicted molecule structures when processing the example molecule data 606 for the example molecule systems.

An example process for training the structure prediction generative model 300 using the training data 602 is described in more detail below with reference to FIG. 7.

In some implementations, the training engine 602 can jointly train the structure prediction generative model 300 with a physics prediction neural network 314 configured to predict molecule properties for molecule systems by processing data characterizing 3D structures for the molecule systems. As one example, the training engine 604 can process predicted molecule properties 614 generated by the physics prediction neural network 314 processing generative model outputs 610 (e.g., layer outputs from a processing layer of the structure prediction generative model that characterize predicted molecule structures) generated by the structure prediction generative model 300 for the example molecule systems of the training data 602. In particular, the objective function for the structure prediction generative model 300 can include a property prediction loss that measures an error between the predicted molecule properties 614 and target molecule properties for the example molecule systems. The training engine 604 can generate parameter updates 616 for the physics prediction neural network 314 and the parameter updates 612 for the structure prediction generative model 300 to reduce (e.g., to optimize) the property prediction loss. For joint training of the structure prediction generative model 300 and the physics prediction neural network 314, the training data 602 can include the target molecule property values for the example molecule systems. As with the target molecule structures for the example molecule systems, the target molecule properties for the example molecule systems can be determined by, e.g., physical experiment, computational simulation, and so on.

As another example, when the structure prediction generative model 300 and the physics prediction neural network 314 share network parameters, the training engine 602 can update (e.g., train) shared portions of the structure prediction generative model 300 as part of training the physics prediction neural network 314 using training data for the physics prediction neural network 314. Training the physics prediction neural network 314 using training data for the physics prediction neural network 314 is described in more detail below with reference to FIG. 6B.

Figure 6B:
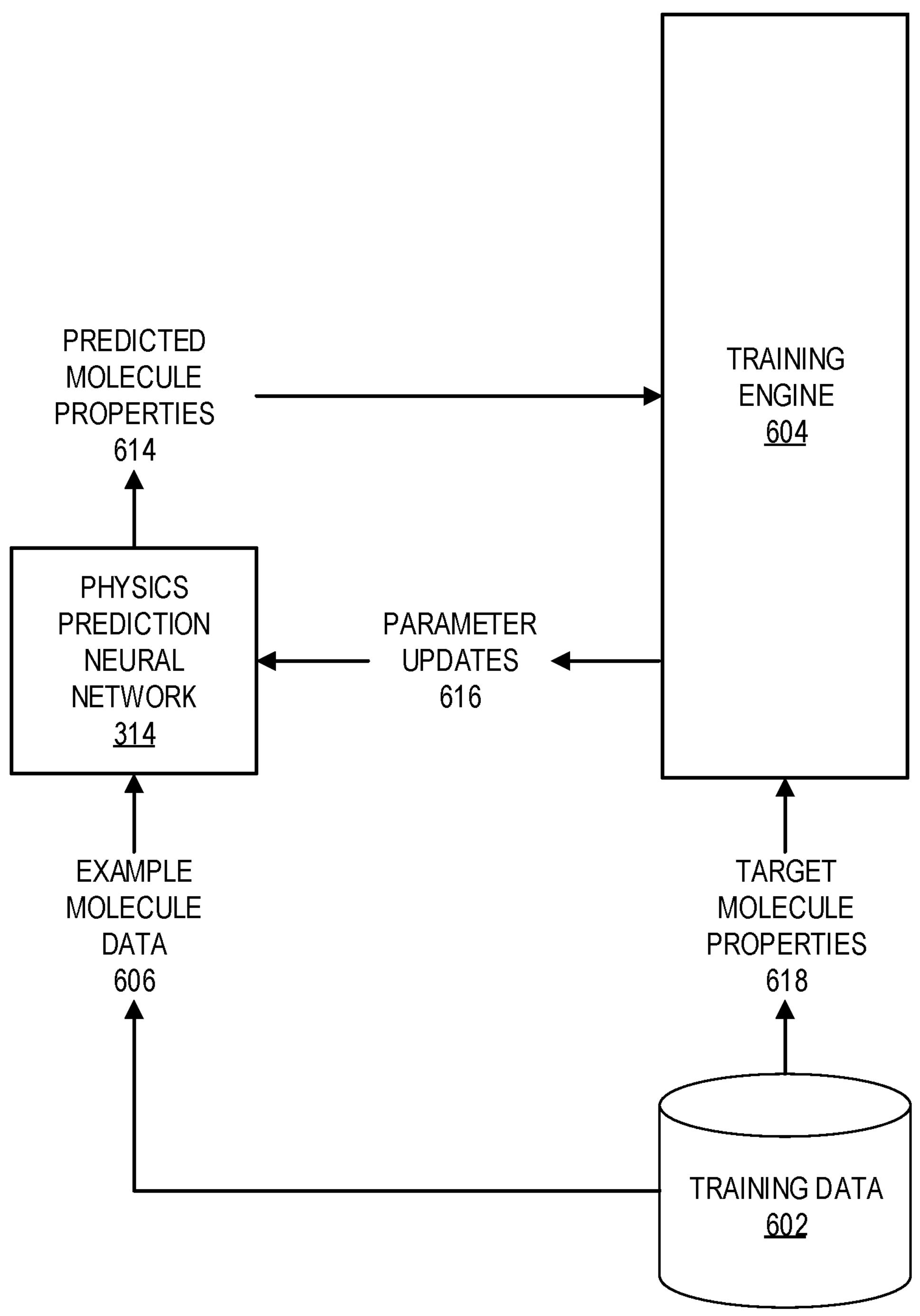
FIG. 6B illustrates training a physics prediction neural network using training data for the physics prediction neural network.

FIG. 6B illustrates training a physics prediction neural network 314 using training data 602 for the physics prediction neural network 314.

The training data 602 for the physics prediction neural network 314 can include example molecule data 606 characterizing 3D structures for each of a plurality of example molecule systems and target molecule properties 618 for each of the example molecule systems. The example molecule systems can be any of a variety of molecule systems, e.g., example proteins, example ligands, example protein-ligand complexes, and so on. The target molecule properties 618 can include any of a variety of molecule properties for the example molecule systems, such as energies of the example molecule systems, atomic forces of the example molecule systems, electron densities of the example molecule systems, and so on. The target molecule properties 618 for the example molecule systems can be determined by any of a variety of means, e.g., by physical experiment with samples of the example molecule systems, by computational simulation of the example molecule systems, and so on.

A training engine 604 can train the physics prediction neural network 314 using the training data 602. In particular, the training engine 604 can determine parameter updates 616 for the physics prediction neural network 314 by processing predicted molecule properties 614 generated by the physics prediction neural network 314 processing the example molecule data 606.

The training engine 604 can generate the parameter updates 616 by evaluating an objective function for the physics prediction neural network 314. In particular, the training engine 604 can generate the parameter updates 616 to optimize the objective function for the physics prediction neural network 314. The objective function for the physics prediction neural network 314 can include a property prediction loss that measures an error between the predicted molecule properties 614 and the target molecule properties 618 for the example molecule systems.

An example process for training the physics prediction neural network 314 using the training data 602 is described in more detail below with reference to FIG. 9.

As described above with reference to FIG. 3, the physics prediction neural network 314 can share network parameters with a structure prediction generative model (e.g., the structure prediction generative model 300 of FIG. 3). For example, the physics prediction neural network 314 can share, e.g., processing layers, blocks, and so on with the structure prediction generative model. By sharing network parameters with the physics prediction neural network 314, portions of the structure prediction generative model can be trained as part of training the physics prediction neural network 314. Sharing network parameters with the physics prediction neural network 314 can therefore increase the amount of training data that can be used to train the structure prediction generative model, as training examples for the physics prediction neural network 314 (e.g., target molecule properties) can often be more easily obtained compared to training examples for the structure prediction generative model (e.g., target 3D structures for molecule systems).

Figure 7:
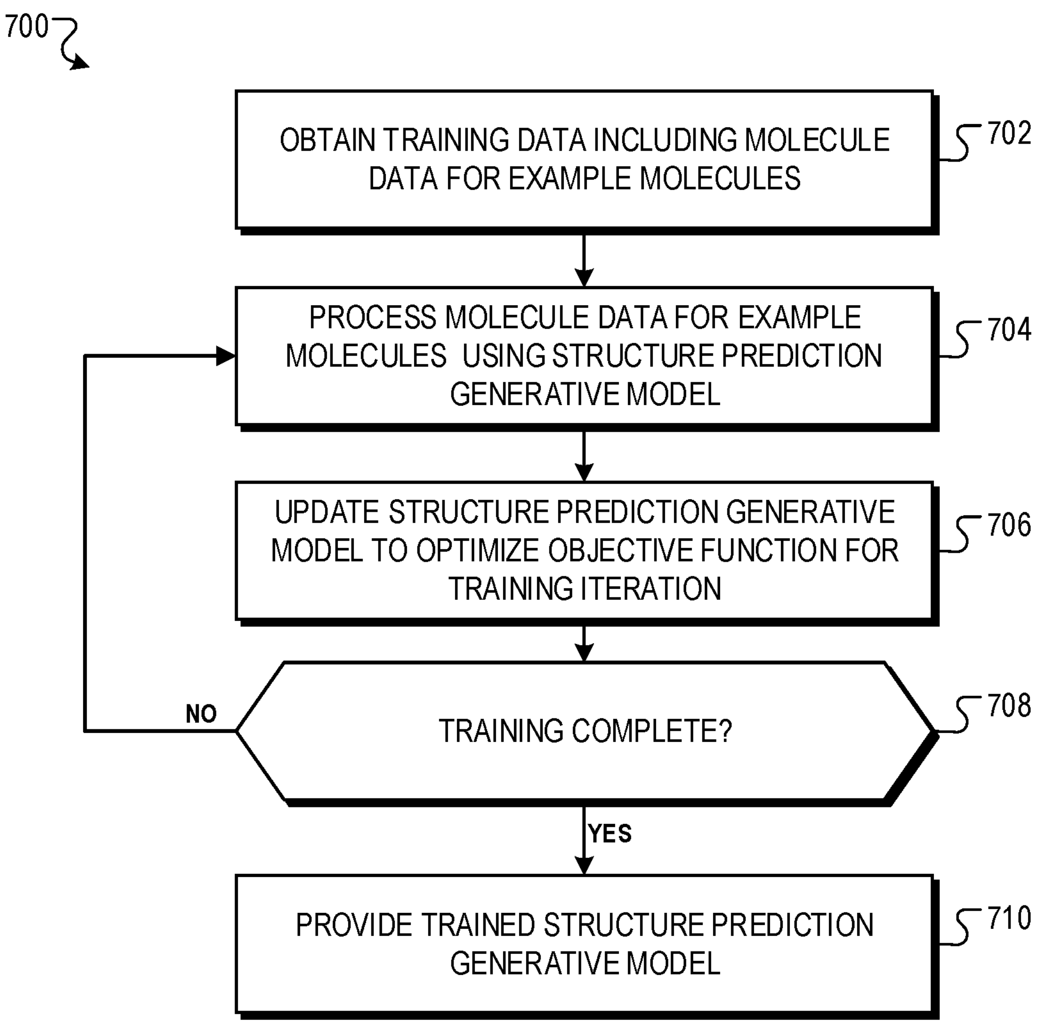
FIG. 7 is a flow diagram of an example process for training a structure prediction generative model.

FIG. 7 is a flow diagram of an example process for training a structure prediction generative model. For convenience, the process 700 will be described as being performed by a system of one or more computers located in one or more locations. For example, a modular structure prediction system, e.g., the modular structure prediction system 100 of FIG. 1, appropriately programmed in accordance with this specification, can perform the process 700.

The system can obtain training data for the structure prediction generative model that includes training examples specifying molecule data for a plurality of example molecule systems (step 702). Each training example can include data characterizing (i) a chemical composition of the example molecule system for the training example and (ii) a target 3D structure for the example molecule system for the training example.

The example molecule systems can be any appropriate type of molecule system for the structure prediction generative model. For example, the example molecule systems can be example proteins when the structure prediction model is a protein generative model, example ligands when the structure prediction model is a ligand generative model, example protein-ligand complexes when the structure prediction model is a protein-ligand generative model, and so on.

The system can obtain the target 3D structures for the example molecule systems from any of a variety of sources. As an example, the training data can include target 3D structures for examples molecule systems as determined by physical experiment (e.g., as determined using x-ray crystallography of physical samples of the example molecule systems, cryo-electron microscopy (cryo-EM) of physical samples of the example molecule systems, and so on). As another example, the training data can include target 3D structures for examples molecule systems as determined by computational simulations (e.g., as determined using molecular dynamics simulations of the example molecule systems, quantum mechanical simulations of the example molecule systems, and so on). In particular, when the example molecule systems are protein-ligand complexes, the target 3D structures for the example molecule systems can be determined using molecular docking computational simulations of the example molecule systems.

In some implementations, the system can obtain the target 3D structures for the example molecule systems from different sources depending on whether the system is pre-training or fine-tuning the structure prediction generative model. For example, when the can obtain target 3D structures determined by computational simulation when pre-training the structure prediction generative model and can obtain target 3D structures determined by physical experiment when fine-tuning the structure prediction generative model. Because computational simulation is less resource intensive compared to performing physical experimentation, pre-training the structure prediction generative model using target molecule structures determined by computational simulation can enable the system pre-train the structure prediction generative model using a larger and more easily obtained training set. Similarly, after pre-training the structure prediction model, the system can fine-tune the structure prediction model using target molecule structures determined by physical experiments can allow the system to efficiently train the structure prediction model using a smaller set of experimentally determined target structures for the example molecule systems.

The system can train the structure prediction generative model over a sequence of training iterations. At each training iteration, the system can perform steps 704 through 708.

The system can process the molecule data for a plurality of training examples for the training iteration using the structure prediction generative model (step 704). For example, the system can process each training example to evaluate a likelihood score (e.g., a log likelihood) for each training example that characterizes a likelihood of the structure prediction generative model producing the target molecule structure for the training example by processing an initial noisy 3D structure for the example molecule system and the molecule data for the example molecule system.

As described above with reference to FIG. 5, the system can be configured to generate predicted 3D structures for molecule systems by iteratively processing (e.g., by iteratively denoising, iteratively transforming, etc.) an initial noisy 3D structure for the molecule systems. For example, the structure prediction generative model can be configured to iteratively denoise an initial 3D structure, $x_0$ over a sequence of denoising iterations, by sampling an updated 3D structure for the i-th denoising iteration from a probability distribution, $p_\theta(x_i|x_{i-1})$ defined by the structure prediction generative model. As another example, the structure prediction generative model can be a flow-based model configured to generate an updated predicted 3D structure for the molecule system for the i-th denoising iteration, $x_i$, using a set of differential equations following:

$$x_i = x_{i-1} + \int_{t_{i-1}}^{t_i} f_\theta(x(t), t)dt$$

Where $f_\theta(x(t),t)$ is configured to predict a rate of change of variables of the molecule structure with respect to a continuous parameter t, $$t, \frac{dx(t)}{dt},$$

that defines a continuous transformation of the predicted structure of the molecule from an initial distribution (e.g., a noise distribution) to a distribution of predicted 3D structures.

As part of determining the likelihood score for each of the training examples, the system can identify an initial noisy 3D structure associated with the target molecule structure for each of the training examples. For example, when the structure prediction generative model is configured to generate a predicted 3D structure for an example molecule system as an output of an N-th denoising iteration, $x_N$, from an initial noisy 3D structure for the example molecule system, $x_0$, the system can identify the noisy 3D structure for the example molecule system for each denoising iteration by iteratively sampling the noisy 3D structures from a predefined noise distribution, $p(x_{i-1}|x_i)$, (e.g., by sampling $x_{N-1} \sim p(x_{N-1}|x_N)$, . . . , $x_0 \sim p(x_0|x_1)$). As another example, when the structure prediction generative model is a flow-based model, the system can identify an initial noisy 3D structure for the example molecule system by determining a reverse transformation defined by the structure prediction generative model, $f^{-1}_\theta(x(t),t)$, and integrating (e.g., numerically integrating) the reverse transformation to obtain:

$$x_0 = x_N + \int_{t_N}^{t_0} f_\theta^{-1}(x(t), t)dt$$

The system can then determine the likelihood score for each of the training examples based on a likelihood of the structure prediction generative model generating the target 3D structures for the training examples, $x_N$, by processing the identified noisy initial 3D structures, $x_0$, for the training examples. For example, when the structure prediction generative model is configured to iteratively denoise the initial 3D structure, $x_0$, over a sequence of denoising iterations, the likelihood score (e.g., log-likelihood) for each training example can be determined following:

$$l(x_N) = \sum_{i=1}^{N} \log p_\theta(x_i \mid x_{i-1})$$

Where $p_\theta(x_i|x_{i-1})$ a likelihood of the structure prediction generative model generating the output of an i-th denoising iteration, $x_i$, conditioned on the noisy 3D structure for the i−1-th iteration, $x_{i-1}$ (e.g., determined by processing the noisy 3D structure, $x_{i-1}$, using the structure prediction generative model, as described above in more detail with reference to FIG. 5).

As another example, when the structure prediction generative model is a flow-based model, the likelihood score (e.g., log-likelihood) for each training example can be determined following:

$$l(x_N) = \log p(x_0) + \int_{t_N}^{t_0} \nabla \cdot f_\theta^{-1}(x(t), t)dt$$

Where $p(x_0)$ is a predetermined distribution for the initial noisy 3D structure $x_0$ and $\nabla \cdot f^{-1}_\theta(x(t),t)$ is a divergence of the reverse transformation with respect to the variables of the molecular structure, x(t).

In particular, when the structure prediction generative model is a flow-based model, the system can determine the likelihood score for each training example by performing a numerical integration of the divergence of the reverse transformation. For example, the system can determine the likelihood score for each training example following:

$$l(x_N) = \log p(x_0) - \sum_{i=0}^{N} (t_i - t_{i-1}) \nabla \cdot f_\theta^{-1}(x(t_i), t_i)$$

In some implementations, as part of processing the molecule data for the training examples of the training iteration, the system can generate one or more predicted 3D structures for each of the example molecules of the training iteration using the structure prediction generative model. For example, as described in more detail below with reference to FIG. 8, the system can generate a plurality of predicted 3D structures for each of the example molecules and can assign alignment scores to each predicted 3D structure that characterizes a physical plausibility of the predicted 3D structure. As another example, as described in more detail below with reference to FIG. 9, the system can generate one or more predicted 3D structures for each of the example molecules and can predict molecule properties for each training example using the predicted 3D structures.

The system can update parameters of the structure prediction generative model to optimize an objective function for the training iteration (step 706). The objective function can include a likelihood loss that measures a likelihood of the structure prediction generative model generating the target 3D structures for the training iteration by processing the example molecule data for the training iteration. For example, when the system evaluates likelihood scores for each training example (e.g., as determined during step 704), the likelihood loss for the training iteration can be a summation of the likelihood scores for each training example of the training iteration. As another example, when the system generates predicted 3D structures for each training example (e.g., as generated during step 704), the likelihood loss for the training iteration can measure a classification accuracy of a discriminator network (e.g., the discriminator neural network for the structure prediction generative model when the structure prediction generative model is a GAN) classifying 3D structures for example molecule systems as either being predicted 3D structures generated by the structure prediction generative model or being target (e.g., ground-truth) 3D structures for the example molecule systems.

The objective function for the training iteration can include any combination of the likelihood loss, an alignment loss (e.g., as determined following the process 800 described below with reference to FIG. 8), and a property prediction loss (e.g., as determined following steps 904 and 906 of the process 900 described below with reference to FIG. 9).

The system can include different loss terms within the objective function depending on whether the system is pre-training or fine-tuning the objective function. For example, the system can pre-train the structure prediction generative model using an objective function that includes only the likelihood loss. As another example, the system can fine-tune the structure prediction generative model using an objective function that includes the property prediction loss, the alignment loss, or both.

As part of updating the parameters of the structure prediction generative model, the system can determine gradients of the objective function (e.g., gradients of the objective function with respect to the parameters of the structure prediction generative model). The system can update the parameters of the structure prediction model using the gradients of the objective function following any appropriate machine learning technique (e.g., following stochastic gradient descent, ADAM, etc.).

The system can determine whether the training is complete (step 708). The system can use any of a variety of criteria to determine whether the training is complete. For example, the system can determine that training is complete after a pre-determined number of training iterations. As another example, the system can determine that training is complete when a value of the objective function falls below a pre-determined threshold. As another example, the system can determine that training is complete when a difference between values of the training objective function for the current training iteration and a previous training iteration falls below a pre-determined threshold.

If the system determines that training is not complete, the system can continue to a next training iteration (e.g., return to step 704)

When the system determines that training is complete, the system can provide the trained structure prediction generative model (step 710).

Figure 8:
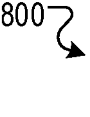
FIG. 8 is a flow diagram of an example process for determining an alignment loss for training a structure prediction generative model.
Figure 8:
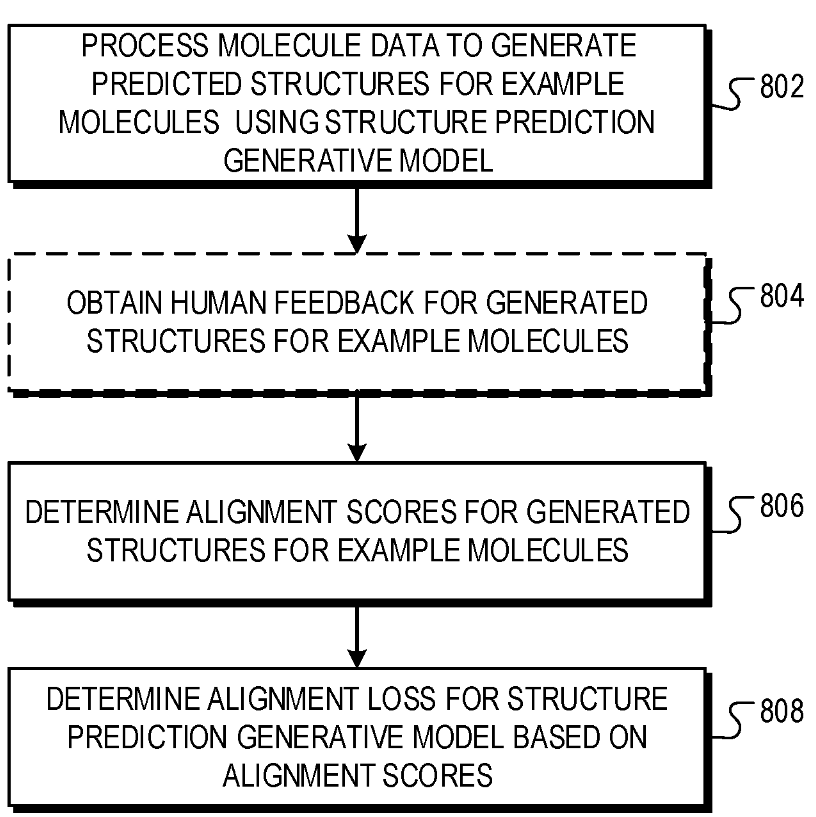

FIG. 8 is a flow diagram of an example process for determining an alignment loss for training a structure prediction generative model. For convenience, the process 800 will be described as being performed by a system of one or more computers located in one or more locations. For example, a training engine, e.g., the training engine 602 of FIG. 6A, appropriately programmed in accordance with this specification, can perform the process 800.

The system can process molecule data for one or more example molecule systems to generate predicted 3D structures for the one or more example molecule systems using the structure prediction generative model (step 802). In particular, the system can use the structure prediction generative model to generate one or more predicted 3D structures for each of the molecule systems following the process 500 of FIG. 5.

The system can generate the predicted 3D structures for the one or more example molecule systems as part of training the structure prediction generative model. In particular, the system can generate the predicted 3D structures for the one or more example molecule systems as part of processing the molecule data for a training iteration of the structure prediction generative model (e.g., as part of perform step 704 described above with reference to FIG. 7).

In some implementations, the system can obtain human (e.g., expert) feedback that characterizes estimated relative likelihoods of the predicted 3D structures for the example molecule systems as determined by human feedback (step 804). For example, the system can provide data characterizing the predicted 3D structures to a user (e.g., an expert), receive human feedback from the user that characterizes estimated relative likelihoods of the predicted 3D structures as estimated by the user, and determine the respective alignment scores for the predicted 3D structures based on the received human feedback. In particular, the system can include a user interface that can provide (e.g., display) the data characterizing the predicted 3D structures to the user and can receive the human feedback as submitted by the user to the user interface.

The human feedback can include data in any of a variety of formats characterizing the estimated relative likelihoods of the predicted 3D structures for the example molecule systems. As an example, the human feedback can include numerical scores assigned by the user to the predicted 3D structures. As another example, the human feedback can include a ranking of the predicted 3D structures as determined by the user.

The system can determine alignment scores for the predicted 3D structures for the example molecule systems (step 806). The alignment score for a predicted 3D structure can characterize a physical plausibility of the predicted 3D structures. In particular, the alignment score for a predicted 3D structure for an example molecule systems can characterize a predicted likelihood of experimentally observing the predicted 3D structure within a physical system that includes the example molecule system.

As an example, when the system obtains human feedback (e.g., following step 804 above), the alignment score for a predicted 3D structure can be, e.g., a ranking, a numerical score, and so on for the predicted 3D structure as assigned by human feedback.

As another example, the alignment score for a predicted 3D structure can characterize an energy of the predicted 3D structure. For example, when the predicted 3D structure is a predicted structure for a protein-ligand complex, the alignment score for the predicted 3D structure can characterize a binding energy between a protein and a ligand of the protein-ligand complex. When the alignment scores characterize energies of the predicted 3D structure, the energies of the predicted 3D structures can be determined by computational simulation (e.g., molecular dynamics simulation, quantum mechanical simulation, etc.) of the predicted 3D structures. In some implementations, the system can determine the energies of the predicted 3D structures by processing data characterizing the predicted 3D structures using a physics prediction neural network (e.g., the physics prediction neural network 314 of FIG. 3). In other implementations, the system can determine the energies of the predicted 3D structures using an energy function (e.g., an energy function that depends on respective bond lengths for a plurality of bonds within the predicted 3D structure).

The system can process the alignment scores for the predicted 3D structures for the example molecule systems to determine an alignment loss (e.g., an alignment objective) for the structure prediction generative model (step 908). The alignment loss can depend on a target distribution of the alignment scores for the predicted 3D structures and can measure an overall physical plausibility of molecule structures generated by the structure prediction generative model.

The target distribution of the alignment scores can be determined by target likelihoods for the predicted 3D structures that depend on both (i) the likelihood of the structure prediction generative model generating the predicted 3D structures and (ii) the alignment score for the predicted 3D structure. For example, the target likelihood, $p^*(x_N)$, for a predicted 3D structure, $x_N$, can be determined following:

$$p^*(x_N) = \frac{1}{Z} p_\theta(x_N) e^{\frac{1}{\beta} S(x_N)}$$

Where $p_\theta(x_N)$ is a likelihood of the structure prediction generative model generating the predicted 3D structure $x_N$ (e.g., an exponentiation of a log-likelihood for the predicted 3D structure $x_N$ determined as described above with reference to step 706 of FIG. 7 above), $S(x_N)$ is the alignment score for the predicted 3D structure $x_N$, $\beta$ is a scaling constant, and Z is a normalizing constant.

The alignment loss (e.g., alignment objective) can measure an error between a first and second ranking of the predicted 3D structures for the training examples. The first ranking can order the predicted 3D structures for the training examples based on respective likelihoods of the structure prediction generative model generating the predicted 3D structures by processing the corresponding example molecule data of the training examples. The second ranking can order the predicted 3D structures for the training examples based on the respective target likelihoods of the predicted 3D structures. For example, when the second ranking assigns K predicted 3D structures an ordering $x^{(1)}, \ldots, x^{(K)}$ (e.g., with $S(x^{(1)}) > \ldots > S(x^{(K)})$), the alignment objective can be a Direct Preference Optimization (DPO) loss defined following:

$$\mathcal{L}_{DPO} = \sum_{k=1}^{K} -\log \frac{e^{\beta \log \frac{p_\theta(x^{(k)})}{p^*(x^{(k)})}}}{\sum_{j=k}^{K} e^{\beta \log \frac{p_\theta(x^{(j)})}{p^*(x^{(j)})}}}$$

Other examples of the Direct Preference Optimization losses are described by Rafailov et al. in "Direct Preference Optimization: Your Language Model is Secretly a Reward Model".

The system can use the alignment loss to train the structure prediction generative model. In particular, the system can update parameters of the structure prediction generative model to optimize an objective function that includes the alignment loss (e.g., following step 706 described above with reference to FIG. 7).

Figure 9:
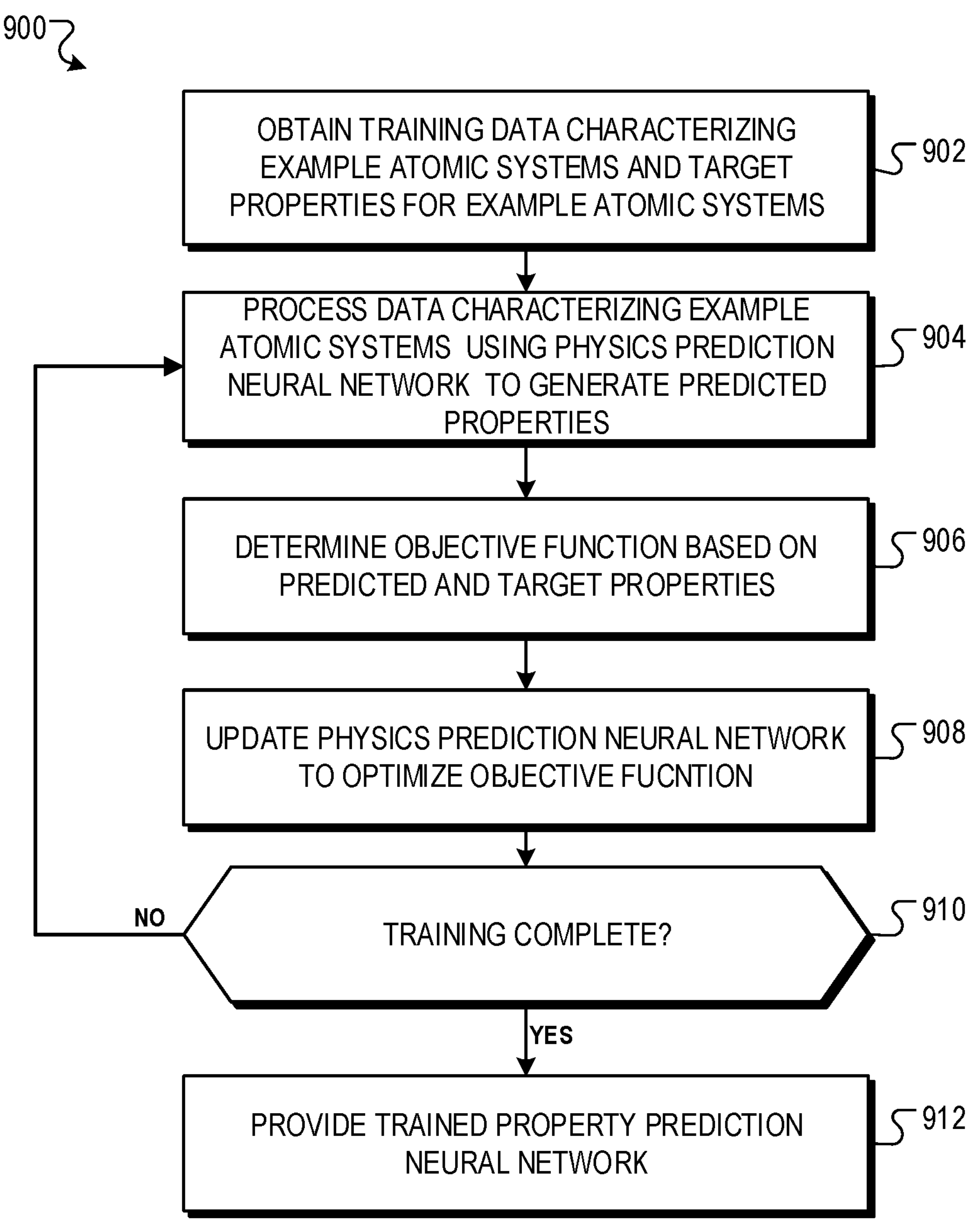
FIG. 9 is a flow diagram of an example process for training a structure prediction generative model.

FIG. 9 is a flow diagram of an example process for training a physics prediction neural network. For convenience, the process 900 will be described as being performed by a system of one or more computers located in one or more locations. For example, a training engine, e.g., the training engine 602 of FIG. 6A, appropriately programmed in accordance with this specification, can perform the process 900.

The system can obtain training data for the property prediction neural network that includes a plurality of physics training examples (step 902). Each physics training example can correspond to a respective example atomic system (e.g., system of atoms) and can include data characterizing: (i) a training network input that characterizes the atomic system for the physics training example and (ii) a target network output that defines one or more target properties of the atomic system for the physics training example. For example, each physics training example can include data characterizing (i) a 3D structure of an example molecule system for the physics training example and (ii) one or more target molecule properties for the example molecule system for the physics training example.

The example molecule systems can be any of a variety of molecule systems, e.g., example proteins, example ligands, example protein-ligand complexes, and so on.

The system can obtain the data specifying the 3D structures for the example molecule systems from any of a variety of sources. As an example, the training data for the physics prediction neural network can include data specifying 3D structures for examples molecule systems as determined by physical experiment (e.g., as determined using x-ray crystallography of physical samples of the example molecule systems, cryo-electron microscopy (cryo-EM) of physical samples of the example molecule systems, etc.), by computational simulations (e.g., as determined using molecular dynamics simulations of the example molecule systems, quantum mechanical simulations of the example molecule systems, etc.), and so on. As another example, in some implementations, the training data for the physics prediction neural network can include data specifying predicted 3D structures as generated by a structure prediction generative model (e.g., as generated following the process 500 of FIG. 5). The structure prediction generative model can generate the predicted 3D structures for the example molecule systems as part of training the structure prediction generative model (e.g., as part of the process 700 of FIG. 7).

The system can train the physics prediction neural network over a sequence of training iterations. At each training iteration, the system can perform steps 904 through 910.

The system can process the training network inputs of one or more physics training examples for the training iteration using the physics prediction neural network to generate respective predicted network outputs that define one or more predicted properties for each of the example atomic systems for the training iteration (step 904). For example, when a physics training example characterizes an example molecule system, the system can process the example 3D structures for example molecule system using the physics prediction neural network to generate one or more predicted molecule properties the example molecule system. The physics prediction neural network can be configured to process data characterizing the example 3D structures for the example molecule systems to predict any of a variety of physical properties of the example molecule systems, e.g., free energy, atomic forces, electron density, and so forth.

The system can evaluate an objective function (e.g., a property prediction loss) for the physics training examples for the training iteration based on the target and the predicted properties for the physics training examples for the training iteration (step 906). For each physics training example, the objective function can measure a discrepancy between (i) the one or more target properties of the atomic system specified by the physics training example and the one or more predicted properties of the atomic system generated by the physics prediction neural network. For example, the objective function can measure a discrepancy (e.g., an L2 loss, a Huber loss, etc.) between target properties for the physics training examples and the predicted properties generated by the physics prediction neural network for the physics training examples.

The system can update parameters of the physics prediction neural network to optimize the objective function for the training iteration (step 908). As part of updating the parameters of the physics prediction neural network, the system can determine gradients of the objective function (e.g., gradients of the property prediction loss with respect to the parameters of the physics prediction neural network). The system can update the parameters of the physics prediction neural network using the gradients of the property prediction loss following any appropriate machine learning technique (e.g., following stochastic gradient descent, ADAM, etc.).

When the physics training examples for the training iteration include predicted 3D structures generated by a structure prediction generative model, the system can update parameters of the structure prediction generative model based on the objective function for the training iteration. In particular, the system can update the parameters of the structure prediction generative model by back propagating gradients of the objective function through the property prediction neural network.

As described in more detail above with reference to FIG. 3, the physics prediction neural network can share network parameters with the structure prediction generative model. The system can therefore update the shared parameters between the physics prediction neural network and the structure prediction generative model as part of updating parameters of the physics prediction neural network to optimize the property prediction loss for the training iteration. Updating the shared parameters between the physics prediction neural network and the structure prediction generative model can enable the system to train portions of the structure prediction generative model using training data for the physics prediction neural network (e.g., without predicting 3D structures for example molecules using the structure prediction generative model).

The system can determine whether the training is complete (step 910). The system can use any of a variety of criteria to determine whether the training is complete. For example, the system can determine that training is complete after a pre-determined number of training iterations. As another example, the system can determine that training is complete when a value of the objective function falls below a pre-determined threshold. As another example, the system can determine that training is complete when a difference between values of the objective function for the current training iteration and a previous training iteration falls below a pre-determined threshold.

If the system determines that training is not complete, the system can continue to a next training iteration (e.g., return to step 904)

When the system determines that training is complete, the system can provide the trained physics prediction neural network (step 912).

Figure 10:
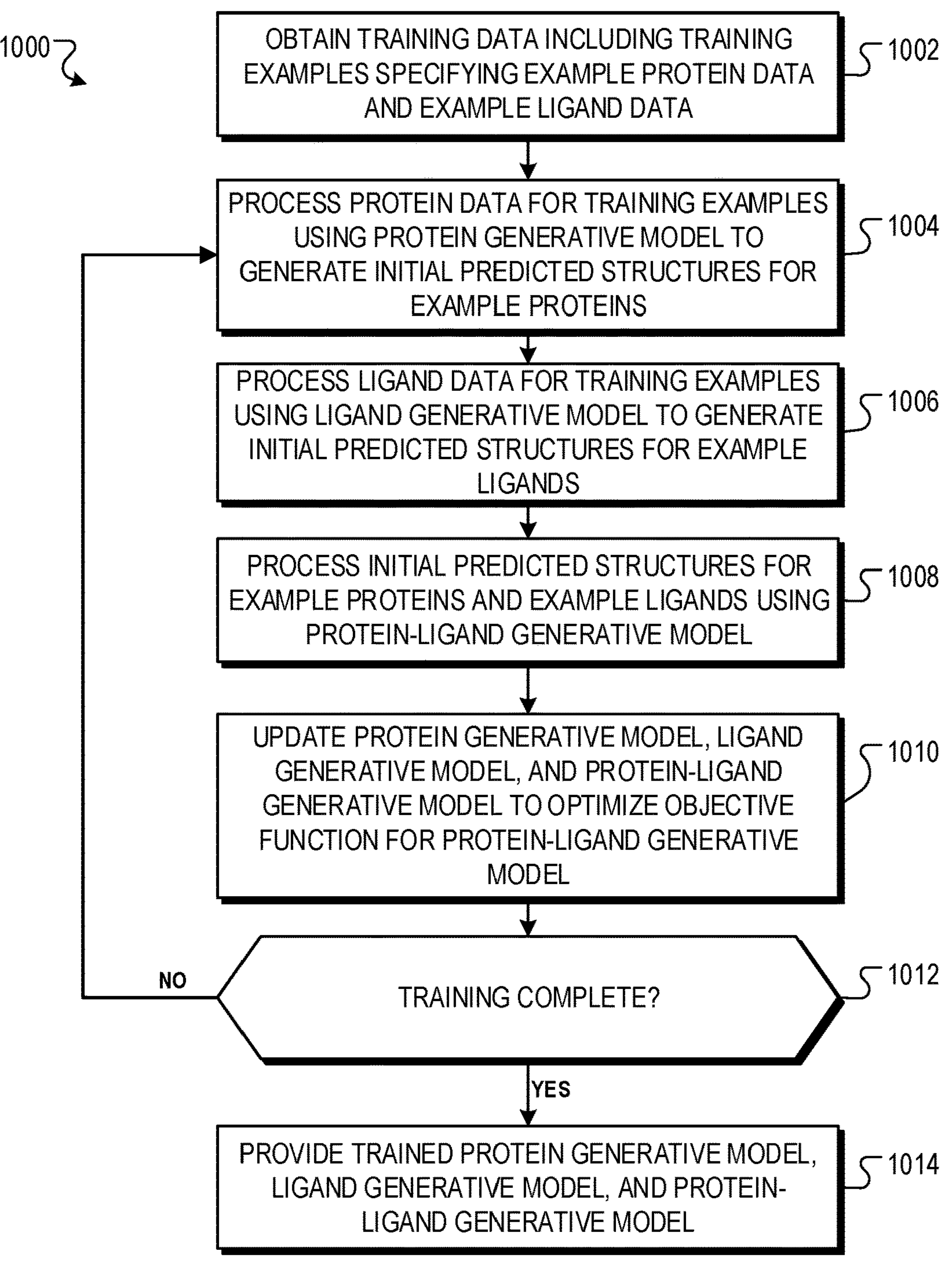
FIG. 10 is a flow diagram of an example process for jointly training a protein generative model, a ligand generative model, and a protein-ligand generative model of a modular structure prediction system.

FIG. 10 is a flow diagram of an example process for jointly training a protein generative model, a ligand generative model, and a protein-ligand generative model of a modular structure prediction system. For convenience, the process 1000 will be described as being performed by a system of one or more computers located in one or more locations. For example, a modular structure prediction system, e.g., the modular structure prediction system 100 of FIG. 1, appropriately programmed in accordance with this specification, can perform the process 1000.

The system can obtain training data that includes training examples specifying example protein data and example ligand data for example protein-ligand complexes for the training examples (step 1002). Each training example can include data characterizing a target 3D structure for the example protein-ligand complex for the training example. The target 3D structures for the example protein-ligand complexes can be obtained by any of a variety of means (e.g., by physical experimentation with physical samples of the example protein-ligand complexes, by computational simulation of the example protein-ligand complexes, and so on).

The system can jointly train the protein generative model, the ligand generative model, and the protein-ligand generative model over a sequence of training iterations. At each training iteration, the system can perform steps 1004 through 1012.

The system can process the protein data for example proteins for the training iteration using the protein generative model to generate initial predicted structures for the example proteins for the training iteration (step 1004). In particular, the protein generative model can generate the initial predicted structures for the example proteins following process 500 of FIG. 5. Prior to joint training with the ligand generative model and the protein-ligand generative model, the protein generative model can be trained (e.g., pre-trained) to generate predicted structures for proteins using training data that includes training examples of example proteins following process 700 of FIG. 7.

The system can process the ligand data for example ligands for the training iteration using the ligand generative model to generate initial predicted structures for the example ligands for the training iteration (step 1006). In particular, the ligand generative model can generate the initial predicted structures for the example ligands following process 500 of FIG. 5. Prior to joint training with the protein generative model and the protein-ligand generative model, the ligand generative model can be trained (e.g., pre-trained) to generate predicted structures for ligands using training data that includes training examples of example ligands following process 700 of FIG. 7.

The system can process the initial predicted structures for the example proteins and example ligands for the training iteration using the protein-ligand generative model (step 1008). In particular, the protein-ligand generative model can process the initial predicted structures for the example proteins and example ligands to determine likelihoods of the protein-ligand generative model generating the target structures for the example protein-ligand complexes as described in more detail with reference to step 704 of FIG. 7. Prior to joint training with the protein generative model and the ligand generative model, the protein-ligand generative model can be trained (e.g., pre-trained) to generate predicted structures for protein-ligand complexes using training data that includes training examples of example protein-ligand complexes following process 700 of FIG. 7.

The system can update parameters of the protein, ligand, and protein-ligand generative models to optimize an objective function for the protein-ligand generative model (step 1010). The objective function can include any combination of a likelihood loss, a property prediction loss, and an alignment loss as determined following step 706 of FIG. 7.

As described in more detail with reference to step 706 of FIG. 7, the system can update the parameters of the protein-ligand generative model using gradients of the objective function with respect to the parameters of the protein-ligand generative model. Similarly, the system can update the parameters of the protein generative model and the parameters of the ligand generative model by backpropagating gradients of the objective function through the protein-ligand generative model.

The system can determine whether the training is complete (step 1012). The system can use any of a variety of criteria to determine whether the training is complete. For example, the system can determine that training is complete after a pre-determined number of training iterations. As another example, the system can determine that training is complete when a value of the objective function falls below a pre-determined threshold. As another example, the system can determine that training is complete when a difference between values of the training objective function for the current training iteration and a previous training iteration falls below a pre-determined threshold.

If the system determines that training is not complete, the system can continue to a next training iteration (e.g., return to step 1004)

When the system determines that training is complete, the system can provide the trained protein, ligand, and protein-ligand generative models (step 1016).

Figure 11:
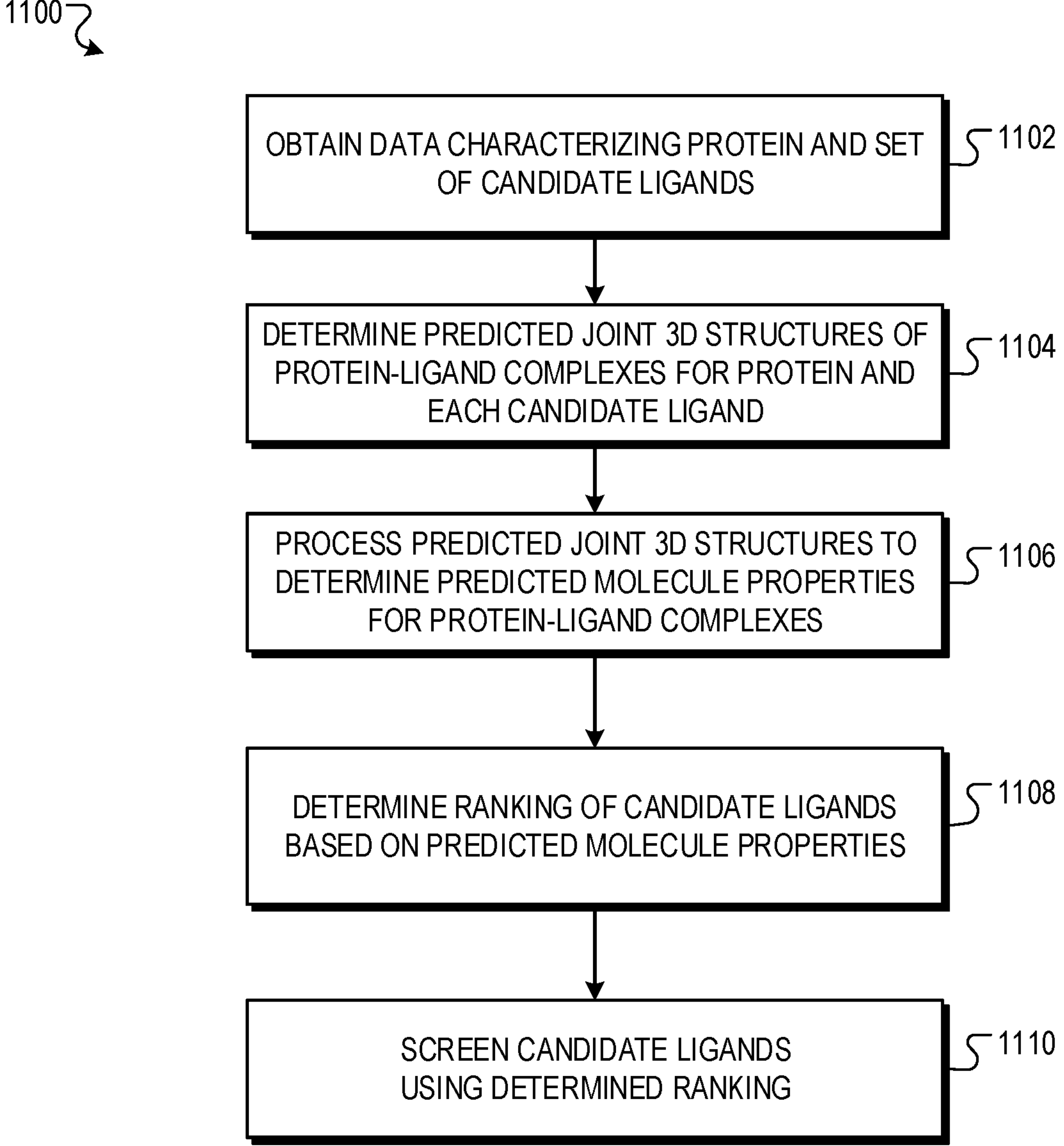
FIG. 11 is a flow diagram of an example process for screening a set of candidate ligands using a modular structure prediction system.

FIG. 11 is a flow diagram of an example process for screening a set of candidate ligands using a modular structure prediction system. For convenience, the process 1100 will be described as being performed by a system of one or more computers located in one or more locations. For example, a modular structure prediction system, e.g., the modular structure prediction system 100 of FIG. 1, appropriately programmed in accordance with this specification, can perform the process 1100.

The system can obtain data characterizing a protein and a set of candidate ligands (e.g., a set of candidate ligands for binding with the protein) (step 1102). The set of candidate ligands can include, e.g., small molecule ligands (e.g., ligands that are non-polymer organic molecules with low molecular weights), poly-peptide ligands (e.g., proteins), nucleic acids (e.g., ribonucleic acids (RNA), deoxyribonucleic acids (DNA), etc.) and so on.

In general, the data characterizing the protein and the set of candidate ligands can specify chemical compositions of the protein and each of the candidate ligands. As an example, the data characterizing the protein and the set of candidate ligands can include data specifying atoms, charges on atoms, bonds, functional groups, amino acids, branches (e.g., from a molecule main chain), ring structures, and so forth within the protein and the candidate ligands. For example, the data characterizing the protein and the set of candidate ligands can include, e.g., Simplified Molecular Input Line Entry System (SMILES) formatted data, International Chemical Identifier (InChI) formatted data, and so on specifying some or all of the protein, the candidate ligands, or both (e.g., specifying compositions molecular components of the protein, the candidate ligands, or both, such as amino acid residues, nucleotides, etc.).

The data characterizing the protein and the set of candidate ligands can specify the chemical composition of the protein by specifying an amino acid sequence for the protein. The amino acid sequence for the protein can specify an identity and an ordering for each of a plurality of amino acid residues within the protein. In some implementations, the data characterizing the protein and the set of candidate ligands can include a respective multiple sequence alignment (MSA) for the proteins characterizing an alignment of a plurality of amino acid sequences associated with the protein. In some implementations, the data characterizing the protein and the set of candidate ligands can include data characterizing known 3D structures (e.g., as determined by physical experiments) for one or more template amino acid sequences for the protein.

Similarly, when a candidate ligand is a protein itself, the data characterizing the protein and the set of candidate ligands can specify the chemical composition of the candidate ligand by specifying an amino acid sequence for the candidate ligand. When a candidate ligand is a protein, the data characterizing the protein and the set of candidate ligands can include, e.g., an MSA for the candidate ligand characterizing an alignment of a plurality of amino acid sequences associated with the candidate ligand, data characterizing known 3D structures for one or more template amino acid sequences for the candidate ligand, and so on.

When a candidate ligand is a nucleic acid, the data characterizing the protein and the set of candidate ligands can specify the chemical composition of the candidate ligand by specifying a nucleotide sequence for the candidate ligand. The nucleotide sequence for the candidate ligand can specify an identity and an ordering for each of a plurality of nucleotides within the candidate ligand.

In some implementations, the data characterizing the protein and the set of candidate ligands can include data characterizing an initial or estimated 3D structure for the protein. The initial or estimated 3D structure of the protein can be determined by any of a variety of means, such as by physical experiment (e.g., x-ray crystallography), by computational simulation (e.g., by molecular dynamics simulations, quantum mechanical simulations, etc.), and so on. As an example, the initial or estimated 3D structure of the protein can be an unfolded or a partially folded structure for the protein. When the data characterizing the protein and the set of candidate ligands characterizes an initial or estimated 3D structure for the protein, the data characterizing the protein and the set of candidate ligands can specify the chemical composition and 3D structure for the protein by specifying a chemical element and a spatial position for each atom of the protein.

Similarly, in some implementations, the data characterizing the protein and the set of candidate ligands can include data characterizing an initial or estimated 3D structures for one or more of the candidate ligands (e.g., as determined by physical experiment, computational simulation, etc.).

The system can determine predicted joint 3D structures for protein-ligand complexes for the protein and each of the set of candidate ligands (step 1104). In particular, the system can determine the predicted joint 3D structures for the protein-ligand complexes by processing the data characterizing the protein and the candidate ligands using a modular structure prediction system following, for each of the candidate ligands, the process 200 described with reference to FIG. 2.

Using the modular structure prediction system, the system can determine the predicted joint 3D structures for the protein-ligand complexes substantially in parallel by loading the data characterizing the protein and the candidate ligands into a local memory of a computing unit (e.g., a graphics processing unit, a tensor processing unit, a central processing unit, an application specific integrated circuit, etc.) and performing the operations of the process 200 of FIG. 2 for each of the candidate ligands substantially in parallel using the computing unit.

Compared to generating individual predicted 3D structures for protein-complexes for each of the candidate ligands in sequence, generating the predicted 3D structures for the protein-ligand complexes for the set of candidate ligands in parallel can significantly reduce the processing time required to determine the predicted 3D structures for the protein-ligand complexes. Additionally, when the system determines the predicted joint 3D structures for the protein-ligand complexes substantially in parallel, the system can transfer data to and from the local memory of the computing unit for all of the candidate ligands in the same memory access operations. Compared to generating individual predicted 3D structures for protein-complexes for each of the candidate ligands in sequence, which can require transferring data to and from the local memory of the computing unit individually (e.g., separately) for each of the candidate ligands, generating the predicted 3D structures for the protein-ligand complexes for the set of candidate ligands in parallel can therefore also reduce the processing time required to determine the predicted 3D structures for the protein-ligand complexes by performing fewer separate transfer operations to and from the local memory of the computing unit.

The system can process the predicted joint 3D structures for the protein-ligand complexes to determine a respective binding score for each of the candidate ligands (step 1106). The binding score for each candidate ligand can characterize a binding affinity of the candidate ligand with the protein.

The system can determine the binding scores for the candidate ligands by any of a variety of means. For example, the system can determine the binding scores for the candidate ligands by computationally simulating the protein-ligand complexes of the protein and the candidate ligands (e.g., by performing molecular dynamics simulations, quantum mechanical simulation, etc.). As another example, the system can determine the binding scores for the candidate ligands by calculating binding affinities for the protein-ligand complexes of the protein and the candidate ligands (e.g., by performing a quantum mechanical calculation of the binding affinities for the protein-ligand complexes based on the predicted structures for the protein-ligand complexes). As another example, the binding scores for the candidate ligands can characterize energies (e.g., binding energies) of the protein-ligand complexes of the protein and the candidate ligands, which the system can determine by processing data characterizing the predicted 3D structures for the protein-ligand complexes using a physics prediction neural network (e.g., the physics prediction neural network 314 of FIG. 3).

The system can determine a ranking of the candidate proteins based on the binding scores for the candidate ligands (step 1108).

The system can use the ranking of the candidate ligands to screen the set of candidate ligands (step 1110). For example, the system can use the ranking of the candidate ligands to screen the candidate ligands for further validation (e.g., by physical experimentation using synthesized samples of selected candidate ligands, computational validation using computational simulation of selected candidate ligands, etc.).

The system can select candidate ligands for the purpose of performing any of a variety of physical experiments and computational simulations for the selected candidate ligands. For example, the system can screen the candidate ligands for the purpose of physically synthesizing the selected candidate ligands to perform physical experiments regarding, e.g., the binding affinities, 3D structures, and so on, of the candidate ligands or of protein-ligand complexes that include the candidate ligands. As another example, the system can screen the candidate ligands for the purpose of physically synthesizing selected candidate ligands to perform physical experiments regarding, e.g., absorption properties, distribution properties, metabolism properties, excretion properties, toxicity properties, and so on of the selected candidate ligands.

As another example, the system can the system can use the ranking of the candidate ligands to select candidate ligands for inclusion within a drug. For example, the system can select a candidate ligand for inclusion within a drug targeting the protein based on the rankings of the candidate ligands determined based on binding scores of the candidate ligands with the protein.

Figure 12:
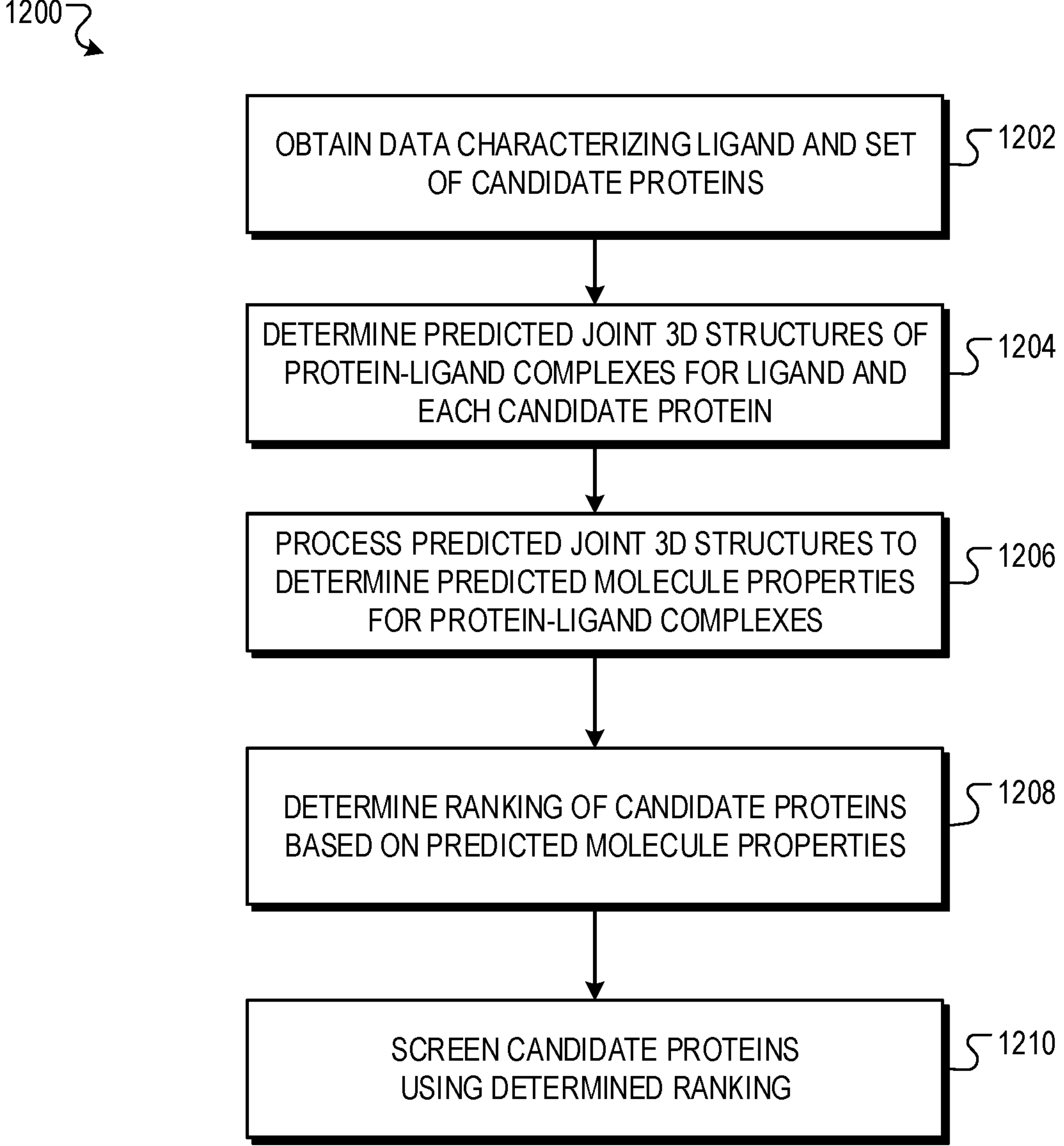
FIG. 12 is a flow diagram of an example process for screening a set of candidate proteins using a modular structure prediction system.

FIG. 12 is a flow diagram of an example process for screening a set of candidate proteins using a modular structure prediction system. For convenience, the process 1200 will be described as being performed by a system of one or more computers located in one or more locations. For example, a modular structure prediction system, e.g., the modular structure prediction system 100 of FIG. 1, appropriately programmed in accordance with this specification, can perform the process 1200.

The system can obtain data characterizing a ligand and a set of candidate proteins (e.g., a set of candidate proteins for binding with the ligand) (step 1202). The ligand can be, e.g., a small molecule ligand (e.g., a ligand that is a non-polymer organic molecule with a low molecular weight), a polypeptide ligand (e.g., a protein), a nucleic acid (e.g., a ribonucleic acid (RNA), a deoxyribonucleic acid (DNA), and so on.

In general, the data characterizing the ligand and the set of candidate proteins can specify chemical compositions of the ligand and each of the candidate proteins. As an example, the data characterizing the ligand and the set of candidate proteins can include data specifying atoms, charges on atoms, bonds, functional groups, amino acids, branches (e.g., from a molecule main chain), ring structures, and so forth within the ligand and the candidate proteins. For example, the data characterizing the ligand and the set of candidate proteins can include, e.g., Simplified Molecular Input Line Entry System (SMILES) formatted data, International Chemical Identifier (InChI) formatted data, and so on specifying some or all of the ligand, the candidate proteins, or both (e.g., specifying compositions molecular components of the ligand, the candidate proteins, or both, such as amino acid residues, nucleotides, etc.).

The data characterizing the ligand and the set of candidate proteins can specify the chemical composition of each candidate protein by specifying an amino acid sequence for the candidate protein. The amino acid sequence for the candidate protein can specify an identity and an ordering for each of a plurality of amino acid residues within the candidate protein. In some implementations, the data characterizing the ligand and the set of candidate proteins can include a respective multiple sequence alignment (MSA) for each of one or more of the candidate proteins characterizing an alignment of a plurality of amino acid sequences associated with the candidate protein. In some implementations, for each of one or more of the candidate proteins, the data characterizing the ligand and the set of candidate proteins can include data characterizing known 3D structures (e.g., as determined by physical experiments) for one or more template amino acid sequences for the candidate protein.

Similarly, when the ligand is a protein itself, the data characterizing the ligand and the set of candidate proteins can specify the chemical composition of the ligand by specifying an amino acid sequence for the ligand. When the ligand is a protein, the data characterizing the ligand and the set of candidate proteins can include, e.g., an MSA for the ligand characterizing an alignment of a plurality of amino acid sequences associated with the ligand, data characterizing known 3D structures for one or more template amino acid sequences for the ligand, and so on.

When the ligand is a nucleic acid, the data characterizing the ligand and the set of candidate proteins can specify the chemical composition of the ligand by specifying a nucleotide sequence for the ligand. The nucleotide sequence for the ligand can specify an identity and an ordering for each of a plurality of nucleotides within the ligand.

In some implementations, the data characterizing the ligand and the set of candidate proteins can include, for each of one or more of the candidate proteins, data characterizing an initial or estimated 3D structure for the candidate protein. The initial or estimated 3D structure of the candidate protein can be determined by any of a variety of means, such as by physical experiment (e.g., x-ray crystallography), by computational simulation (e.g., by molecular dynamics simulations, quantum mechanical simulations, etc.), and so on. As an example, the initial or estimated 3D structure of the candidate protein can be an unfolded or a partially folded structure for the candidate protein. When the data characterizing the ligand and the set of candidate proteins characterizes an initial or estimated 3D structure for a candidate protein, the data characterizing the ligand and the set of candidate proteins can specify the chemical composition and 3D structure for the candidate protein by specifying a chemical element and a spatial position for each atom of the candidate protein.

Similarly, in some implementations, the data characterizing the ligand and the set of candidate proteins can include data characterizing an initial or estimated 3D structure for the ligand (e.g., as determined by physical experiment, computational simulation, etc.).

The system can determine predicted joint 3D structures for protein-ligand complexes for the ligand and each of the set of candidate proteins (step 1204). In particular, the system can determine the predicted joint 3D structures for the protein-ligand complexes by processing the data characterizing the ligand and the candidate proteins using a modular structure prediction system following, for each of the candidate proteins, the process 200 described with reference to FIG. 2.

Using the modular structure prediction system, the system can determine the predicted joint 3D structures for the protein-ligand complexes substantially in parallel by loading the data characterizing the ligand and the candidate proteins into a local memory of a computing unit (e.g., a graphics processing unit, a tensor processing unit, a central processing unit, an application specific integrated circuit, etc.) and performing the operations of the process 200 of FIG. 2 for each of the candidate proteins substantially in parallel using the computing unit.

Compared to generating individual predicted 3D structures for protein-complexes for each of the candidate proteins in sequence, generating the predicted 3D structures for the protein-ligand complexes for the set of candidate proteins in parallel can significantly reduce the processing time required to determine the predicted 3D structures for the protein-ligand complexes. Additionally, when the system determines the predicted joint 3D structures for the protein-ligand complexes substantially in parallel, the system can transfer data to and from the local memory of the computing unit for all of the candidate proteins in the same memory access operations. Compared to generating individual predicted 3D structures for protein-complexes for each of the candidate proteins in sequence, which can require transferring data to and from the local memory of the computing unit individually (e.g., separately) for each of the candidate proteins, generating the predicted 3D structures for the protein-ligand complexes for the set of candidate proteins in parallel can therefore also reduce the processing time required to determine the predicted 3D structures for the protein-ligand complexes by performing fewer separate transfer operations to and from the local memory of the computing unit.

The system can process the predicted joint 3D structures for the protein-ligand complexes to determine a respective binding score for each of the candidate proteins (step 1206). The binding score for each candidate protein can characterize a binding affinity of the candidate protein with the ligand.

The system can determine the binding scores for the candidate proteins by any of a variety of means. For example, the system can determine the binding scores for the candidate proteins by computationally simulating the protein-ligand complexes of the ligand and the candidate proteins (e.g., by performing molecular dynamics simulations, quantum mechanical simulation, etc.). As another example, the system can determine the binding scores for the candidate proteins by calculating binding affinities for the protein-ligand complexes of the ligand and the candidate proteins (e.g., by performing a quantum mechanical calculation of the binding affinities for the protein-ligand complexes based on the predicted structures for the protein-ligand complexes). As another example, the binding scores for the candidate proteins can characterize energies (e.g., binding energies) of the protein-ligand complexes of the ligand and the candidate proteins, which the system can determine by processing data characterizing the predicted 3D structures for the protein-ligand complexes using a physics prediction neural network (e.g., the physics prediction neural network 314 of FIG. 3).

The system can determine a ranking of the candidate proteins based on the binding scores for the candidate proteins (step 1208).

The system can use the ranking of the candidate proteins to screen the set of candidate proteins (step 1210). For example, the system can use the ranking of the candidate proteins to screen the candidate proteins for further validation (e.g., by physical experimentation using synthesized samples of selected candidate proteins, computational validation using computational simulation of selected candidate proteins, etc.).

The system can select candidate proteins for the purpose of performing any of a variety of physical experiments and computational simulations for the selected candidate proteins. For example, the system can screen the candidate proteins for the purpose of physically synthesizing the selected candidate proteins to perform physical experiments regarding, e.g., the binding affinities, 3D structures, and so on, of the candidate proteins or of protein-ligand complexes that include the candidate proteins.

As another example, the system can the system can use the ranking of the candidate proteins to select the ligand for inclusion within a drug. For example, the system can identify that the ligand binds with a screened candidate protein (e.g., based on the based on the rankings of binding scores of the candidate proteins with the ligand) and can select the ligand for inclusion within a drug targeting the screened candidate protein.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, or a Jax framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:

training a generative model by a machine learning training technique using an alignment objective, comprising, at each of a sequence of training steps:

obtaining data characterizing a set of one or more molecules for the training step;

processing, by the generative model and in accordance with current values of a set of generative model parameters of the generative model, the data characterizing the set of one or more molecules for the training step to generate a plurality of alternative predicted 3D structures of the set of one or more molecules for the training step;

determining a current alignment score distribution over the plurality of alternative predicted 3D structures, wherein the current alignment score distribution defines a respective current alignment score for each of the plurality of alternative predicted 3D structures that is based at least in part on a likelihood of the generative model generating the alternative predicted 3D structure;

determining a target alignment score distribution over the plurality of alternative predicted 3D structures, wherein the target alignment score distribution defines a respective target alignment score for each of the plurality of alternative predicted 3D structures, comprising, for each of the plurality of alternative predicted 3D structures:

processing the alternative predicted 3D structure using an energy model to determine a predicted potential energy of the set of one or more molecules in a conformation characterized by one or more structure parameters of the alternative predicted 3D structure;

determining the target alignment score for the alternative predicted 3D structure based at least in part on the predicted potential energy of the alternative predicted 3D structure;

training the set of generative model parameters of the generative model to optimize the alignment objective, wherein the alignment objective measures a discrepancy between: (i) the current alignment score distribution over the plurality of alternative predicted 3D structures, and (ii) the target alignment score distribution over the plurality of alternative predicted 3D structures; and providing the trained generative model.

2. The method of claim 1, wherein for each of the plurality of alternative predicted 3D structures of the set of one or more molecules for the training step:

the target alignment score for the alternative predicted 3D structure is determined based on both: (i) the likelihood of the generative model generating the alternative predicted 3D structure and (ii) the predicted potential energy of the alternative predicted 3D structure.

3. The method of claim 1, wherein for each alternative predicted 3D structure, the likelihood of the generative model generating the alternative predicted 3D structure characterizes a likelihood of the generative model generating the alternative predicted 3D structure by processing the data characterizing the set of one or more molecules for the training step in accordance with values of an initial set of generative model parameters.

4. The method of claim 1, wherein the alignment objective measures an error between a first ranking and a second ranking of the plurality of alternative predicted 3D structures of the set of one or more molecules for the training step, wherein:

the first ranking orders the plurality of alternative predicted 3D structures based on the current alignment score distribution; and the second ranking orders the plurality of alternative predicted 3D structures based on the target alignment score distribution.

5. The method of claim 4, wherein training the set of generative model parameters of the generative model to optimize the alignment objective comprises:

determining a gradient of the alignment objective with respect to the current values of the set of generative model parameters; and updating the current values of the set of generative model parameters based on the gradient of the alignment objective.

6. The method of claim 1, wherein:

the set of one or more molecules collectively define a protein-ligand complex; and the prediction potential energy of each alternative predicted 3D structure characterizes a binding energy of the protein-ligand complex.

7. The method of claim 1, wherein for each alternative predicted 3D structure, determining the predicted potential energy of the alternative predicted 3D structure comprises simulating the alternative predicted 3D structure to determine the predicted potential energy of the alternative predicted 3D structure.

8. The method of claim 1, wherein for each of the plurality of alternative predicted 3D structures of the set of one or more molecules for the training step, the target alignment score for the alternative predicted 3D structure is based on both: (i) the predicted potential energy of the alternative predicted 3D structure, and (ii) human feedback regarding the alternative predicted 3D structure.

9. The method of claim 8, further comprising obtaining human feedback regarding the plurality of alternative predicted 3D structures by performing operations comprising:

outputting data characterizing the plurality of alternative predicted 3D structures to a user;

receiving human feedback from the user that characterizes estimated relative likelihoods of the predicted 3D structures.

10. The method of claim 9, wherein the human feedback comprises numerical scores assigned by the user to the alternative predicted 3D structures.

11. The method of claim 9, wherein the human feedback comprises a ranking of the alternative predicted 3D structures as determined by the user.

12. The method of claim 1, wherein the data characterizing the set of one or more molecules for the training step characterizes a respective chemical composition of each molecule in the set of one or more molecules.

13. The method of claim 1, wherein the set of one or more molecules for the training step includes a protein.

14. The method of claim 13, wherein the data characterizing the set of one or more molecules for the training step includes an amino acid sequence of the protein.

15. The method of claim 1, wherein the set of one or more molecules for the training step includes a ligand.

16. The method of claim 15, wherein the data characterizing the set of one or more molecules for the training step includes a chemical structure of the ligand.

17. A system comprising:

one or more computers; and one or more storage devices communicatively coupled to the one or more computers, wherein the one or more storage devices store instructions that, when executed by the one or more computers, cause the one or more computers to perform operations comprising:

training a generative model by a machine learning training technique using an alignment objective, comprising, at each of a sequence of training steps:

obtaining data characterizing a set of one or more molecules for the training step;

processing, by the generative model and in accordance with current values of a set of generative model parameters of the generative model, the data characterizing the set of one or more molecules for the training step to generate a plurality of alternative predicted 3D structures of the set of one or more molecules for the training step;

determining a current alignment score distribution over plurality of alternative predicted 3D structures, wherein the current alignment score distribution defines a respective current alignment score for each of the plurality of alternative predicted 3D structures that is based at least in part on a likelihood of the generative model generating the alternative predicted 3D structure;

determining a target alignment score distribution over the plurality of alternative predicted 3D structures, wherein the target alignment score distribution defines a respective target alignment score for each of the plurality of alternative predicted 3D structures, comprising, for each of the plurality of alternative predicted 3D structures;

processing the alternative predicted 3D structure using an energy model to determine a predicted potential energy of the set of one or more molecules in a conformation characterized by one or more structure parameters of the alternative predicted 3D structure;

determining the target alignment score for the alternative predicted 3D structure based at least in part on the predicted potential energy of the alternative predicted 3D structure;

training the set of generative model parameters of the generative model to optimize the alignment objective, wherein the alignment objective measures a discrepancy between: (i) the current alignment score distribution over the plurality of alternative predicted 3D structures, and (ii) the target alignment score distribution over the plurality of alternative predicted 3D structures; and providing the trained generative model.

18. One or more non-transitory computer storage media storing instructions that when executed by one or more computers cause the one or more computers to perform operations comprising:

training a generative model by a machine learning training technique using an alignment objective, comprising, at each of a sequence of training steps:

obtaining data characterizing a set of one or more molecules for the training step;

processing, by the generative model and in accordance with current values of a set of generative model parameters of the generative model, the data characterizing the set of one or more molecules for the training step to generate a plurality of alternative predicted 3D structures of the set of one or more molecules for the training step;

determining a current alignment score distribution over the plurality of alternative predicted 3D structures, wherein the current alignment score distribution defines a respective current alignment score for each of the plurality of alternative predicted 3D structures that is based at least in part on a likelihood of the generative model generating the alternative predicted 3D structure;

determining a target alignment score distribution over the plurality of alternative predicted 3D structures, wherein the target alignment score distribution defines a respective target alignment score for each of the plurality of alternative predicted 3D structures, comprising, for each of the plurality of alternative predicted 3D structures;

processing the alternative predicted 3D structure using an energy model to determine a predicted potential energy of the set of one or more molecules in a conformation characterized by one or more structure parameters of the alternative predicted 3D structure;

determining the target alignment score for the alternative predicted 3D structure based at least in part on the predicted potential energy of the alternative predicted 3D structure;

training the set of generative model parameters of the generative model to optimize the alignment objective, wherein the alignment objective measures a discrepancy between: (i) the current alignment score distribution over the plurality of alternative predicted 3D structures, and (ii) the target alignment score distribution over the plurality of alternative predicted 3D structures; and providing the trained generative model.

19. The non-transitory computer storage media of claim 18, wherein for each of the plurality of alternative predicted 3D structures of the set of one or more molecules for the training step:

the target alignment score for the alternative predicted 3D structure is determined based on both: (i) the likelihood of the generative model generating the alternative predicted 3D structure and (ii) the predicted potential energy of the alternative predicted 3D structure.

20. The non-transitory computer storage media of claim 18, wherein for each alternative predicted 3D structure, the likelihood of the generative model generating the alternative predicted 3D structure characterizes a likelihood of the generative model generating the alternative predicted 3D structure by processing the data characterizing the set of one or more molecules for the training step in accordance with values of an initial set of generative model parameters.

* * * * *